(12) United States Patent
Baird et al.

(10) Patent No.: US 6,916,618 B2
(45) Date of Patent: Jul. 12, 2005

(54) ISOLATION OF THE LAMIN γ2 GENE IN HORSES AND ITS USE IN DIAGNOSTIC JUNCTIONAL EPIDERMOLYSIS BULLOSA

(75) Inventors: John Baird, Guelph (CA); Keith Linder, Raleigh, NC (US); Guerrino Meneguzzi, Nice (FR); Flavia Spirito, Nice (FR); Alexandra Charlesworth, Nice (FR)

(73) Assignees: University of Guelph, Ontario (CA); Institut National de la Santé et de la Recherche Médicale, Paris (FR)

( * ) Notice: Subject to any disclaimer, the term of this patent is extended or adjusted under 35 U.S.C. 154(b) by 30 days.

(21) Appl. No.: 10/053,662

(22) Filed: Jan. 24, 2002

(65) Prior Publication Data

US 2003/0143545 A1 Jul. 31, 2003

(51) Int. Cl.⁷ .................................................. C12Q 1/68
(52) U.S. Cl. ............................. 435/6; 435/15; 530/350
(58) Field of Search ...................... 435/6, 15; 530/350

(56) References Cited

U.S. PATENT DOCUMENTS 5,660,982 A * 8/1997 Tryggvason et al. ........... 435/6
6,265,168 B1 * 7/2001 Gjerde et al. .................. 435/6

OTHER PUBLICATIONS

Bruckner–Tuderman L. et al., (1991) *J Invest Dermatol.* 96 :452–458.
Engel, J. et al., (1991) *Biochem Soc Trans.* 19 :839–843.
Fine, J.D. et al., (2000) *J Am Acad Dermatol.* 42 :1051–1066.
Fuchs, E. (1992) *J Invest Dermatol.* 99 :671–674.
Gache, Y., et al., (1996) *J Clin Invest.* 97 :2289–2298.
Gagnoux–Palacios, L. et al., (2001) *J Cell Biol.* 153 :835–850.
Heida, Y. et al., (1992) *J Cell Biol.* 116 :1497–1506.
Kallunki, P. et al., (1992) *J Cell Biol.* 119 :679–693.
Markinkovic, M.P. et al., (1992) *J Biol Chem.* 267 :17900–17906.
Pulkkinen, L. et al., (1999) *Matrix Biol.* 18 :29–42.
Salo, S., et al., (1999) *Matrix Biol.* 18 :197–210.
Sambrook, J., et al., (1989) A Laboratory Manual.
Sonneberg, A., et al., (1987) *J Biol Chem.* 262 :10376–10383.
Sugiyama, S., et al., (1995) *Eur J Biochem.* 228:120–128.
Uitto, J., et al., (1993) *Semin Dermatol* 12 :191–201.
Vailly, J., et al., (1994) *Eur J Biochem* 219 :209–218.
Vidal, F., et al., (1995) *Nat Genet.* 10 :229–234.

* cited by examiner

*Primary Examiner*—Robert A. Wax
(74) *Attorney, Agent, or Firm*—Ogilvy Renault; Susan Tandan

(57) ABSTRACT

The laminin γ2 subunit of equine laminin-5 gene has been cloned and the nucleic acid and corresponding protein amino acid sequence is provided. A method of diagnosing junctional epidermolysis bullosa in horses is also provided based on the determination that a mutation in the laminin γ2 gene in which a cytosine is inserted at position 1368 is associated with the disease.

6 Claims, 7 Drawing Sheets

(3 of 7 Drawing Sheet(s) Filed in Color)

```
                                                           5'TGGGTCCTCCTTATTCACAGG    -177
TGAGTCACACCCTGAAACACAGGCTCTCTTCCTGTCAGGACTGAGTCAGGTAGAAGAGTCGATAAAACCACCTGATCAAGGAAAAG   -91
GAAGGCACAGCGGAGCGCAGAGTGAGAACTCCCAGCGGCGAGGCGCCGGGCAGCGACCCCTGCAGCGGCGGACCGCGCGCCGGCCTGGCC  -1
ATGCCTGCGCTCTGGCTGAGCTGCTACCTCTGCTTCTCGCTCCTCCTGCCCGCAGCCCGGGCCACCTCCGGGAGGGAAGTCTGTGATTGC   90
 M  P  A  L  W  L  S  C  Y  L  C  F  S  L  L  L  P  A  A  R  A  T  S  G  R  E  V  C  D  C    30
                                                        ↑            ├──
                                                                      Dom V
AACGGGAAGTCCAGGCAATGCATCTTTGACCAGGAACTTCACAAACAGACAGGAAATGGATTCCGCTGCCTCAACTGCAATGACAACACT  180
 N  G  K  S  R  Q  C  I  F  D  Q  E  L  H  K  Q  T  G  N  G  F  R  C  L  N  C  N  D  N  T    60

GATGGCATCCACTGCGAGAGGTGCAAGGCAGGATTTTACCGACAGAGAGAAAGGGACCGCTGTTTACCCTGCAATTGTAACTCTAAAGGT  270
 D  G  I  H  C  E  R  C  K  A  G  F  Y  R  Q  R  E  R  D  R  C  L  P  C  N  C  N  S  K  G    90

TCTCTTAGCGCTCGATGTGACAACTCTGGACGGTGCAGCTGTAAGCCAGGTGTGACAGGAGACAGGTGTGACCGATGTCTGCCCGGCTTC  360
 S  L  S  A  R  C  D  N  S  G  R  C  S  C  K  P  G  V  T  G  D  R  C  D  R  C  L  P  G  F   120

CACACACTCACTGATGCTGGGTGCGCCCAAGACCAAAGGCTGCTAGACTCCAAGTGTGACTGTGACCCAGCTGGCATCTCAGGGCCCTGT  450
 H  T  L  T  D  A  G  C  A  Q  D  Q  R  L  L  D  S  K  C  D  C  D  P  A  G  I  S  G  P  C   150

GACTCAGGCCGCTGTGTCTGCAAGCCGGCTGTCACTGGAGAGCGCTGTGATAGGTGTCGACCAGGTTACTATCACCTGGATGGGGGAAAC  540
 D  S  G  R  C  V  C  K  P  A  V  T  G  E  R  C  D  R  C  R  P  G  Y  Y  H  L  D  G  G  N   180

CCTCAGGGCTGTACCCAGTGTTTTTGCTATGGGCATTCCGCCAGCTGCCACAGCTCTGGGGACTACAGTGTCCATAAAATCATCTCTGCC  630
 P  Q  G  C  T  Q  C  F  C  Y  G  H  S  A  S  C  H  S  S  G  D  Y  S  V  H  K  I  I  S  A   210
                                         ├──→
                                          dom. IV
TTCCATCAAGATGTTGATGGCTGGAAGGCTGTCCAAAGAAACGGGTCTCCTGCAAAGCTCCAGTGGTCACAGCGCCATCGGGATATATTT  720
 F  H  Q  D  V  D  G  W  K  A  V  Q  R  N  G  S  P  A  K  L  Q  W  S  Q  R  H  R  D  I  F   240

AGCTCAGCACGACGATCAGACCCTGTCTATTTTGTAGCTCCTGCCAAATTTCTTGGGAATCAACAGGTGAGCTACGGGCAAAGCCTATCT  810
 S  S  A  R  R  S  D  P  V  Y  F  V  A  P  A  K  F  L  G  N  Q  Q  V  S  Y  G  Q  S  L  S   270

TTTGACTACCGTGTGGATAGGGGAGGCAGACACCCATCTGCCCATGACGTGATCCTGGAAGGTGCTGGTCTACGGATCACAGCTCCCTTG  900
 F  D  Y  R  V  D  R  G  G  R  H  P  S  A  H  D  V  I  L  E  G  A  G  L  R  I  T  A  P  L   300

ATGCCACTTAGCAAGACACTGCCTTGTGGGATCACCAAGACTTACACATTCAGATTAAATGAACATCCAAGCAGTAATTGGAGCCCCCAG  990
 M  P  L  S  K  T  L  P  C  G  I  T  K  T  Y  T  F  R  L  N  E  H  P  S  S  N  W  S  P  Q   330

CTAAGTTACTTTGAGTATCGGAGGTTACTGCGGAACCTCACAGCCCTGCGGATCCGAGCTACCTACGGAGAATACAGTACTGGGTACATT 1080
 L  S  Y  F  E  Y  R  R  L  L  R  N  L  T  A  L  R  I  R  A  T  Y  G  E  Y  S  T  G  Y  I   360

GACAACGTGACCTTGATTTCAGCCCGCCCCGTTTCTGGAGCCCCAGCGCCCTGGGTTGAACAATGTGTATGCCCTGTTGGCTACAAGGGG 1170
 D  N  V  T  L  I  S  A  R  P  V  S  G  A  P  A  P  W  V  E  Q  C  V  C  P  V  G  Y  K  G   390
                                                        ├──→
                                                         Dom. III
CAGTTCTGCCAGGATTGTGCTTCCGGCTACAAAAGAGATTCAGCCAGACTGGGACCTTTTGGCACCTGTATTCCATGTAACTGCCAAGGG 1260
 Q  F  C  Q  D  C  A  S  G  Y  K  R  D  S  A  R  L  G  P  F  G  T  C  I  P  C  N  C  Q  G   420

GGAGGGGCCTGCGATCCAGACACAGGAGACTGTTACTCAGGGGATGAGAACCCTGACATCCCTGAGTGTGCTGACTGCCCCATTGGTTTC 1350
 G  G  A  C  D  P  D  T  G  D  C  Y  S  G  D  E  N  P  D  I  P  E  C  A  D  C  P  I  G  F   450

TACAACGATCCACAAGACCCCCGCAGCTGCAAGCCGTGCCCCTGTCGCAATGGGTTCAGCTGCTCCGTGATGCCTGAGACAGAGGAGGTG 1440
 Y  N  D  P  Q  D  P  R  S  C  K  P  C  P  C  R  N  G  F  S  C  S  V  M  P  E  T  E  E  V   480

GTGTGCAATAACTGCCCCCAGGGTGTCACTGGTGCCCGCTGTGAGCTCTGTGCTGATGGCTATTTTGGGGACCCCTTCGGGGAACGTGGC 1530
 V  C  N  N  C  P  Q  G  V  T  G  A  R  C  E  L  C  A  D  G  Y  F  G  D  P  F  G  E  R  G   510

CCAGTGAGGCCTTGTCAGCCCTGTCAGTGCAACAACAACGTGGACCCTAGTGCCTCCGGGAACTGTGACCGCCTGACAGGCAGGTGTCTG 1620
 P  V  R  P  C  Q  P  C  Q  C  N  N  N  V  D  P  S  A  S  G  N  C  D  R  L  T  G  R  C  L   540

AAGTGCATCCACAACACAGCTGGGGTCCACTGTGACCAGTGCAAAGCAGGCTACTATGGGGACCCGTTGGCTCCCAATCCAGCAGACAAG 1710
 K  C  I  H  N  T  A  G  V  H  C  D  Q  C  K  A  G  Y  Y  G  D  P  L  A  P  N  P  A  D  K   570

TGTCGAGCTTGCAACTGCAACCCAGTGGGCTCGGAGCCTGTGGAGTGTCGAAGTGATGGCAGCTGTGTTTGCAAGCCAGGCTTTGGTGGC 1800
 C  R  A  C  N  C  N  P  V  G  S  E  P  V  E  C  R  S  D  G  S  C  V  C  K  P  G  F  G  G   600
```

FIG. 3A

```
CTCAGCTGTGAGCATGCGGCACTGACCAGCTGTCCAGCTTGCTATAATCAAGTGAAGGTTCAGATGGATCAGTTTATGCAGCAGCTCCAG 1890
 L  S  C  E  H  A  A |L  T  S  C  P  A  C  Y  N  Q  V  K  V  Q  M  D  Q  F  M  Q  Q  L  Q   630
                     └───▶Dom. I/II
ATCCTGGAGGCCCTGATTTCGAAGGCTCAGGGTGGAGCAGTACCCAACGCAGAGCTGGAAGGCAGGATGCAGCAGGCTGAGCAGGCCCTT 1980
 I  L  E  A  L  I  S  K  A  Q  G  G  A  V  P  N  A  E  L  E  G  R  M  Q  Q  A  E  Q  A  L   660

CGGGACATTCTGAGAGAAGCCCAGATTTCACAAGATGCTGTTAGATCCTTCAATCTCCGGGTGGCCAAGGCAAGGACTCAAGAGAATAGC 2070
 R  D  I  L  R  E  A  Q  I  S  Q  D  A  V  R  S  F  N  L  R  V  A  K  A  R  T  Q  E  N  S   690

TACCGGGACCGCCTGGATGACCTCAAGATGACTGTGGAAAGAGTTCGGGCCCTGGGCAGTCAGTATCAGAACCAAGTTCAGGATACTCGC 2160
 Y  R  D  R  L  D  D  L  K  M  T  V  E  R  V  R  A  L  G  S  Q  Y  Q  N  Q  V  Q  D  T  R   730

AGGCTCATCACTCAGATGCGCCTGAGCCTGGAGGAAAGTGAGGCTTCCCTGCAAAACACCAACATTCCTCCTTCAGAGCACTACGTGGGG 2250
 R  L  I  T  Q  M  R  L  S  L  E  E  S  E  A  S  L  Q  N  T  N  I  P  P  S  E  H  Y  V  G   750

CCAAATGGCTTTAAAAGTCTGGCTCAGGAGGCCACGAGATTGGCAGACAGCCATGTTCAGTCAGCCAGTAACATGGAGCAACTGGCAAAG 2340
 P  N  G  F  K  S  L  A  Q  E  A  T  R  L  A  D  S  H  V  Q  S  A  S  N  M  E  Q  L  A  K   780

GAAACCCAGGAGTATTCCAAAGAGCTGATGTCACTGGTGCGCGAGGCTCTGCAGGAAGGAGGCGGAAGCGGCAGCCTGGACGGAGCCGTG 2430
 E  T  Q  E  Y  S  K  E  L  M  S  L  V  R  E  A  L  Q  E  G  G  G  S  G  S  L  D  G  A  V   810

GTGCAAAGGCTTGTGGGAAAATTGCAGAAAACTAAATCTCTGGCCCAGGAGTTGTCGAGGGAGGCCACGCAAACCGACATGGAAGCAGAT 2520
 V  Q  R  L  V  G  K  L  Q  K  T  K  S  L  A  Q  E  L  S  R  E  A  T  Q  T  D  M  E  A  D   840

AGGTCTTATCAGCATAGTCTCCACCTTCTCAATTCCGTGTCTCAGATTCAGGGAGTCAATGATCAGTCCTTGCAGGTAGAAGCGAAGAGG 2610
 R  S  Y  Q  H  S  L  H  L  L  N  S  V  S  Q  I  Q  G  V  N  D  Q  S  L  Q  V  E  A  K  R   870

CTCAGACAAAAAGCTGATTCTCTCTCAAACCGTGTGACTAAGCATATGGATGAGTTCAAGCACGTGCAAAGCAATCTGGGAAACTGGGAA 2700
 L  R  Q  K  A  D  S  L  S  N  R  V  T  K  H  M  D  E  F  K  H  V  Q  S  N  L  G  N  W  E   900

GAAGAAACCCGGCAGCTCTTACAGAATGGAAAGAATGGGAGACAGACATCAGATCAGCTGCTTTCCCGTGCCAACCTTGCTAAAAGCAGA 2790
 E  E  T  R  Q  L  L  Q  N  G  K  N  G  R  Q  T  S  D  Q  L  L  S  R  A  N  L  A  K  S  R   930

GCCCAAGAAGCACTAAGTATGGGCAATGCCACTTTTTATGAAGTTGAGAACATCTTAAAGAATCTCAGAGAGTTTGACCTGCAGGTTGGA 2880
 A  Q  E  A  L  S  M  G |N  A  T| F  Y  E  V  E  N  I  L  K  N  L  R  E  F  D  L  Q  V  G   960

GATAAAAGAGCAGAAGCTGAAGAGGCCATGAAGAGACTCTCCTACATCAGCCAGAAGGTTGCAGGTGCCAGTGACAAGACGAAGCAAGCA 2970
 D  K  R  A  E  A  E  E  A  M  K  R  L  S  Y  I  S  Q  K  V  A  G  A  S  D  K  T  K  Q  A   990

GAAGCAGCCCTGGGCAGTGCTGCTGCCGACGCCCAGAGGGCAAAGAATGCAGCCAGGGAGGCCCTGGAGATCTCTGGCAAGATAGAACAG 3060
 E  A  A  L  G  S  A  A  A  D  A  Q  R  A  K  N  A  A  R  E  A  L  E  I  S  G  K  I  E  Q  1020

GAGATAGGAGGTCTGAACTTGGAAGCCAATGTGACAGCAGATGGAGCCTTGGCCATGGAGAAGGGACTGGCCACTCTGAAAAGTGAGATG 3150
 E  I  G  G  L  N  L  E  A |N  V  T| A  D  G  A  L  A  M  E  K  G  L  A  T  L  K  S  E  M  1050

AGAGAAGTGGAAGGAGAGCTGTCAAGGAAGGAGCAGGAGTTTGACATGGATATGGACGCAGTGCAGATGGTAATTGCAGAGGCCCAAAGA 3240
 R  E  V  E  G  E  L  S  R  K  E  Q  E  F  D  M  D  M  D  A  V  Q  M  V  I  A  E  A  Q  R  1080

GTTGAAAACAGAGCCAAGAATGCTGGAGTTACGATCCAAGACACACTCAACACATTGGATGGCATCCTACACCTAATAGACCAGCCTGGC 3330
 V  E  N  R  A  K  N  A  G  V  T  I  Q  D  T  L  N  T  L  D  G  I  L  H  L  I  D  Q  P  G  1110

AGTGTGGATGAAGAGAGGCTGATCTTACTGGAGCAGAAGCTTTTCCGAGCCAAGACTCAGATCAACAGCCAGCTACGGCCCTTGATGTCA 3420
 S  V  D  E  E  R  L  I  L  L  E  Q  K  L  F  R  A  K  T  Q  I  N  S  Q  L  R  P  L  M  S  1140

GAGCTGGAAGAGAGGGCACATCGGCAGAAGGGCCACCTCCGTTTCCTGGAGACTAGCATAGATGGGATTCTGGCTGATGTGAAGAACCTG 3510
 E  L  E  E  R  A  H  R  Q  K  G  H  L  R  F  L  E  T  S  I  D  G  I  L  A  D  V  K  N  L  1170

GAGAACATCAGGGACAACCTGCCCCCGGGCTGCTACAATACCCAGGCTCTTGAGCAACAGtgaagctgccttagagatttctcaaccaag 3600
 E  N  I  R  D  N  L  P  P  G  C  Y  N  T  Q  A  L  E  Q  Q  *                                1190
gttcttgggattcagacctagctgccttagagatttctcaaccaaggttcttgggattcagacctcagggctcaggagcccgcatgcggg 3690
tggggtgggatgggaatatttgaatatgttgaatgcgtgtgctcaggccccagtgaacctgatcccatccctgagacctcggccagataa 3780
atgtctttattg                                                                             3789-3'
```

FIG. 3B

```
horse    1     MPALWLSCYLCFSLLLPAARATSGREVCDCNGKSRQCIFDQELHKQTGNGFRCLNCNDNTDGIHCERCKAGFYRQRERDRCLPCNCNSKGSLSARCDNSG
man      1     MPALWLGCCLCFSLLLPAARATSRREVCDCNGKSRQCIFDRELHRQTGNGFRCLNCNDNTDGIHCEKCKNGFYRHRERDRCLPCNCNSKGSLSARCDNSG
mouse    1     MPALWLSCCLGVALLLPASQATSRREVCDCNGKSRQCVFDQELHRQAGSGFRCLNCNDNTAGVHCERSREGFYQHQSKSRCLPCNCHSKGSLSAGCDNSG horse    101   RCSCKPGVTGDRCDRCLPGFHTLTDAGCAQDQRLLDSKCDCDPAGISGPCDSGRCVCKPAVTGERCDRCRPGYYHLDGGNPQGCTQCFCYGHSASCHSSG
man      101   RCSCKPGVTGARCDRCLPGFHMLTDAGCTQDQRLLDSKCDCDPAGIAGPCDAGRCVCKPAVTGERCDRCRSGYYNLDGGNPEGCTQCFCYGHSASCRSSA
mouse    101   QCRCKPGVTGQRCDQCQPGFHMLTDAGCTRDQGQLDSKCDCDPAGISGPCDSGRCVCKPAVTGERCDRCRPRDYHLDRANPEGCTQCFCYGHSASCHASA horse    201   DYSVHKIISAFHQDVDGWKAVQRNGSPAKLQWSQRHRDIFSSARRSDPVYFVAPAKFLGNQQVSYGQSLSFDYRVDRGGRHPSAHDVILEGAGLRITAPL
man      201   EYSVHKITSTFHQDVDGWKAVQRNGSPAKLQWSQRHQDVFSSAQRLDPVYFVAPAKFLGNQQVSYGQSLSFDYRVDRGGRHPSAHDVILEGAGLRITAPL
mouse    201   DFSVHKITSTFSQDVDGWKAVQRNGAPAKLHWSQRHRDVFSSARRSDPVYFVAPAKFLGNQQVSYGQSLSFDYRVDRGGRQPSAYDVILEGAGLQIRAPL horse    301   MPLSKTLPCGITKTYTFRLNEHPSSNWSPQLSYFEYRRLLRNLTALR-IRATYGEYSTGYIDNVTLISARPVSGAPAPWVEQCVPVGYKGQFCQDCASG
man      301   MPLGKTLPCGLTKTYTFRLNEHPSNNWSPQLSYFEYRRLLRNLTALR-IRATYGEYSTGYIDNVTLISARPVSGAPAPWVEQCICPVGYKGQFCQDCASG
mouse    301   MAPGKTLPCGITKTYTFRLNEHPSSHWSPQLSYFEYRRLLRNLTALLMIRATYGEYSTGYIDNVTLVSARPVLGAPAPWVERCVCLLGYKGQFCQECASG horse    400   YKRDSARLGPFGTICIPCNCQGGGACDPDTGDCYSGDENPDIPECADCPIGFYNDPQDPRSCKPCPCRNGFSCSVMPETEEVVCNNCPQGVTGARCELCAD
man      400   YKRDSARLGPFGTICIPCNCQGGGACDPDTGDCYSGDENPDI-ECADCPIGFYNDPHDPRSCKPCPCHNGFSCSVMPETEEVVCNNCPPGVTGARCELCAD
mouse    401   YKRDSARLGAFGACVPCNCQGEGACDPDTGDCYSGDENPDI-ECADCPIGFYNDPHDPRSCKPCPCHNGFSCSVMPETEEVVCNNCPPGVTGARCELCAD horse    500   GYFGDPFGERGPVRPCQPCQNCNNNVDPSASGNCDRLTGRCLKCIHNTAGVHCDQCKAGYYGDPLAPNPADKCRACNCNPVGSEPVECRSDGSCVCKPFG
man      499   GYFGDPFGEHGPVRPCQPCQCNNNVDPSASGNCDRLTGRCLKCIHNTAGIYCDQCKAGYFGDPLAPNPADKCRACNCNPMGSEPVGCRSDGTCVCKPFG
mouse    500   GFFGDPFGEHGPVRPCQRCQNCNNNVDPNASGNCDQLTGRCLKCIYNTAGVYCDQCKAGYFGDPLAPNPADKCRACNCSPMGAEPGECRGDGSCVCKPFG horse    600   GLSCEHAALTSCPACYNQVKVQMDQFMQQLQILEALISKAQGG---AVPNAELEGRMQQAEQALRDILREAQISQDAVRSFNLRVAKARTQENSYRDRLD
man      599   GPNCEHGAFS-CPACYNQVKIQMDFMQQLQRMEALISKAQGGDG-VVPDTELEGRMQQAEQALQDILRDAQISEGASRSLGLQLAKVRSQENSYQSRLD
mouse    600   AFNCDHAALTSCPACYNQVKIQMDFTQQLQSLEALVSKAQGGGGGTPVQLEGRIEQAEQALQDILGEAQISEGAMRAVAVRLAKARSQENDYKTRLD horse    697   DLKMTVERVRALGSQYQNQVQDTIRRLITQMRLSLEESEASLQNTNIPPSEHYVGPNGFKSLAQEATRLADSHVQSASNMEQLAKETQEYSKELMSLVREA
man      697   DLKMTVERVRALGSQYQNRVRDTHRLITQMQLSLAESEASLGNTNIPASDHYVGPNGFKSLAQEATRLAESHVESASNMEQLTRETEDYSKQALSLVRKA
mouse    700   DLKMTAERIRALGSQHQNRVQDTSRLISQMRLSLAGSEALLENTNIHSSEHYVGPNDFKSLAQEATRKADSHAESANAMKQLARETEDYSKQALSLARKL horse    797   LQE---GGGSGSLDGAVVQRLVGKLQKTKSLAQELSREATQTDMEADRSYQHSLHLLNSVSQIQGVNDQSLQVEAKR-LRQKADSLSNRVTKHMDEFKHVQ
man      797   LHEGVGSGSGSPDGAVVQGLVEKLEKTKSLAQQLTREATQAEIEADRSYQHSLRLLDSVSRLQGVSDQSFQVEEAKRIRQKADSLSTLVTRHMDEFKRTQ
mouse    800   LSG---GGGSGSWDSSVVQGLMGKLEKTKSLSQQLSLEGTQADIEADRSYQHSLRLLDSASQLQGVSDLSFQVEAKR-IRQKADSLSNLVTRQTDAFTRVR horse    894   SNLGNWEEETRQLLQNGKNGRQTSDQLLSRANLAKSRAQEALSMGNATFYEVENILKNLREFDLQVGDKRAEAEEAMKRLSYISQKVAGASDKTKQAEAA
man      897   KNLGNWKEEAQQLLQNGKSGREKSDQLLSRANLAKSRAQEALSMGNATFYEVESILKNLREFDLQVDNRKAEAEEAMKRLSYISQKVSDASDKTQQAERA
mouse    897   NNLGNWEKETRQLLQTGKDRRQTSDQLLSRANLAKNRAQEALSMGNATFYEVENILKNLREFDLQVEDRKAEAEEAMKRLSSISQKVADASDKTQQAETA horse    994   LGSAAADAQRAKNAAREALEISGKIEQEIGGLNLEANVTADGALAMEKGLATLKSEMREVEGELSRKEQEFDMDMDAVQMVIAEAQRVENRAKNAGVTIQ
man      997   LGSAAADAQRAKNGAGEALEISSEIEQEIGSLNLEANVTADGALAMEKGLASLKSEMREVEGELERKELEFDTNMDAVQMVITEAQKVDTRAKNAGVTIQ
mouse    997   LGSATADTQRAKNAAREALEISSEIELEIGSLNLEANVTADGALAMEKGTATLKSEMREMI-ELARKELEFDTVQLVITEAQQADARATSAGVTIQ horse    1094  DTLNTLDGILHLIDQPGSVDEERLILLEQKLFRAKTQINSQLRPLMSELEERAHRQKGHLRLFLETSIDGILADVKNLENIRDNLPPGCYNTQALEQQ
man      1097  DTLNTLDGLLHLMDQPLSVDEEGLVLLEQKLSRAKTQINSQLRPMMSELEERARQQRGHLHLLETSIDGILADVKNLENIRDNLPPGCYNTQALEQQ
mouse    1096  DTLNTLDGILHLIDQPGSVDEEGMMLLEQGLFQAKTQINSRLRPLMSDLEERVRRQRNHLHLLETSIDGILADVKNLENIRDNLPPGCYNTQALEQQ
```

ISOLATION OF THE LAMIN γ2 GENE IN HORSES AND ITS USE IN DIAGNOSTIC JUNCTIONAL EPIDERMOLYSIS BULLOSA

FIELD OF THE INVENTION

The present invention relates to the isolation of the gene encoding the γ2 subunit of equine laminin-5 and its use in diagnosing junctional epidermolysis bullosa (JEB) in horses.

BACKGROUND OF THE INVENTION

Epidermolysis bullosa (EB) is a group of hereditary and acquired diseases of the skin and mucous membranes that share the common feature of the formation of blisters and erosions in response to minor trauma (Fine et al., 2000).

In humans, the clinical forms of hereditary EB are divided into three main categories, each typified by the level of skin separation within the dermal-epidermal basement membrane zone and by the proteins involved. EB simplex (EBS) is characterized by separation occurring in the basal keratinocytes due to mutations in the keratin 5 and 14 genes or in the hemidesmosomal component plectin (Fuchs, 1992). In dystrophic EB (DEB), the skin separates at the lower layer of the basement membrane zone, the lamina densa, as a result of defects in anchoring fibrils (Uitto and Christiano, 1993). In junctional EB (JEB), blister formation takes place within the lamina lucida of the dermal-epidermal basement membrane and several mutations have been described in the three genes (LAMA3, LAMB3, and LAMC2) that encode the anchoring filament protein, laminin 5, and the two transmembrane components of the hemidesmosome (HD), collagen XVII and integrin α6β4. Among the JEB variants, the non-Herlitz or mild forms of JEB (non-H JEB) are characterized by chronic and localized blistering with non-shortening of the patient's life span. Hemidesmosomes are present but usually reduced in number. Herlitz JEB (H-JEB) represents the most severe and the most frequent form of JEB (greater than 50% of cases). H-JEB is characterized by generalized blistering with erosions of the skin and mucous membranes, and is lethal in early childhood. Ultrastructural and immunohistochemical observations demonstrate abnormalities in hemidesmosome anchoring filaments complexes. Immunostaining of the skin of patients affected by H-JEB reveals absence of laminin-5.

Laminin 5 is synthesized within the basal epithelial cells as a heterotrimeric molecule composed of an α3 (200 kDa), a β3 (140 kDa) and a γ2 (155 kDa) chain that associate to form a triple-stranded α-helical coiled-coil rod domain (Engel, 1991). A large number of distinct mutations (greater than 100) have been identified in the three genes encoding the polypeptide subunits of laminin 5 (Pulkkinen and Uitto, 1999).

Animal models for mechanobullous disorders have been described in the literature, including transgenic mouse models and xenograft models but naturally-occurring, well-characterized animal models are rare.

Clinical reports of sporadic cases of hereditary EB have been described in a range of animals including sheep (Bruckner-Tuderman), cattle, cats, dogs and horses, but electron microscopy examination was often absent, the breeding history of animals incomplete and the inheritance mode of the disease unclear. Clinical features observed in humans often differ in animals and this is probably due to differences in the skin characteristics among species.

In order to understand the molecular basis of this disease in horses, with a view to minimizing its occurrence, it would be desirable to clone the relevant genes in an attempt to determine the cause of one or more forms of EB in horses.

SUMMARY OF THE INVENTION

In one aspect of the present invention, an isolated polynucleotide encoding the γ2 subunit of laminin-5 in horses is provided.

In another aspect of the present invention, a method for diagnosing JEB in horses is provided comprising the steps of:

1) obtaining a biological sample from a horse;
2) isolating nucleic acid from the sample and amplifying laminin γ2-encoding polynucleotide using appropriate primers; and
3) sequencing the laminin γ2-encoding polynucleotide, wherein an inserted cytosine at position 1368 is indicative of JEB.

In another aspect of the present invention, there is provided a method of diagnosing JEB in horses comprising:

1) obtaining a biological sample from a horse;
2) isolating protein from the sample; and
3) screening the sample for laminin-γ2 peptide, wherein an absence of laminin-γ2 in the sample is indicative of JEB.

In a further aspect of the present invention, a kit for diagnosing JEB in horses is provided. The kit includes the primers, 5'-TGTTACTCAGGGGATGAGAA-3' (SEQ ID No: 29) and (antisense) 5'-CTGGGGGCAGTTATTGCAC-3' (SEQ ID No: 30) for use in amplifying laminin γ2 nucleic acid.

These and other aspects of the present invention are described by reference to the following figures in which:

BRIEF DESCRIPTION OF THE FIGURES

The claim of this patent contains at least one drawing executed in color.

FIG. 3 illustrates the nucleotide (SEQ ID No: 1) and deduced amino acid (SEQ ID No: 2) sequence of the horse laminin γ2 chain;

FIG. 4. Direct comparison of the primary structure of the horse (upper line), human (middle line) and mouse (lower line) laminin γ2 chain;

DETAILED DESCRIPTION OF THE INVENTION

Figure 1:
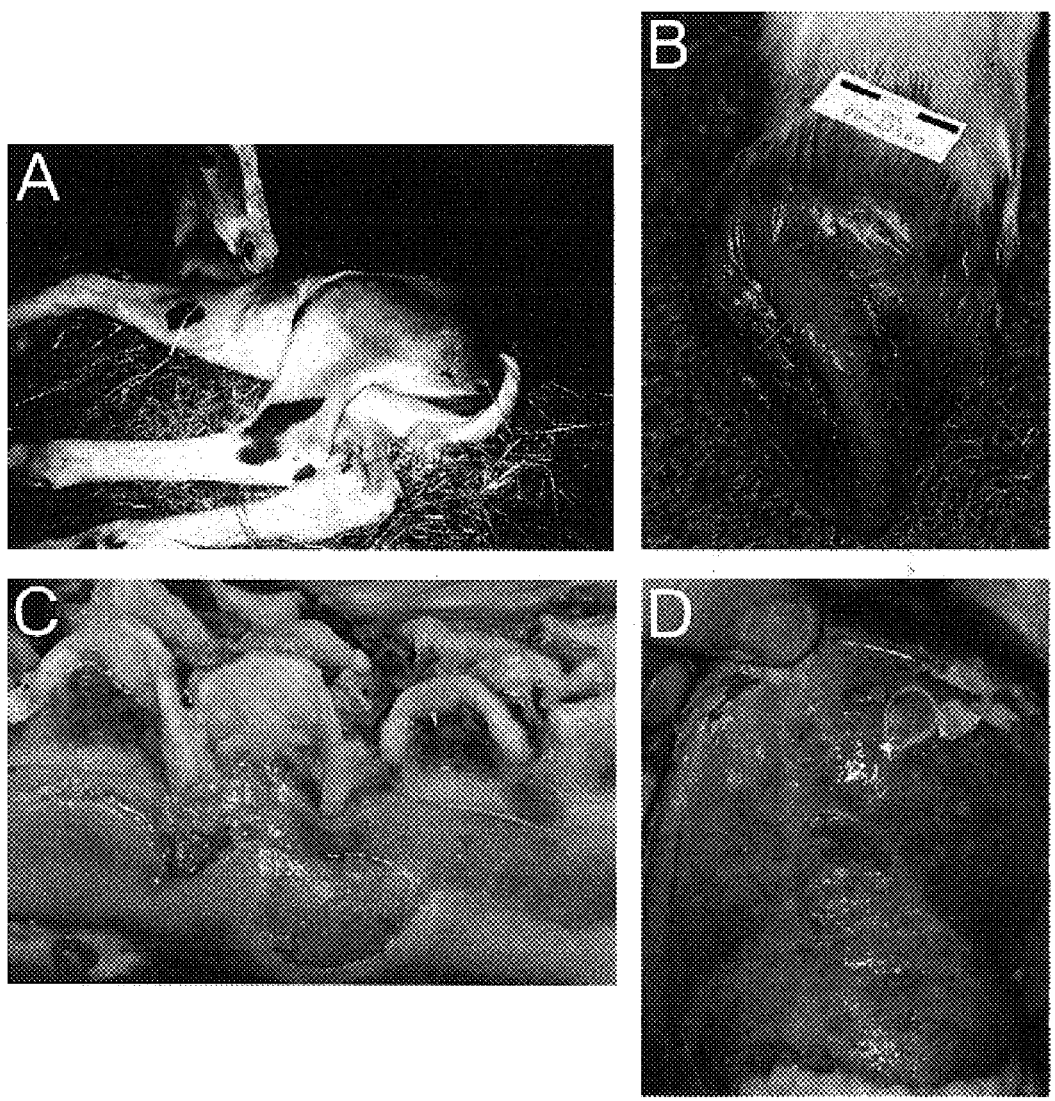
FIG. 1 illustrates the clinical features of JEB in Belgian horses.

Junctional epidermolysis bullosa (JEB) in horses has been linked to the γ2 subunit of the laminin-5 gene. A γ2-encoding polynucleotide has been cloned and sequenced in accordance with an aspect of the present invention. The mutation associated with the clinical signs of JEB in horses results in a homozygous nucleotide insertion in the laminin γ2-encoding polynucleotide, a frame shift, and a premature termination codon. Specifically, a cytosine insert occurs in the genomic nucleic acid sequence of affected horses at position 1368 of the laminin γ2-encoding polynucleotide.

As used herein, the term "laminin γ2" is meant to refer to the "γ2" or "LAMC2" subunit of the anchoring filament protein, laminin-5.

The isolated laminin γ2 polynucleotide comprises a 3570-bp full-length open reading frame, the sequence of which is set out in SEQ ID NO: 1 (FIG. 3). The polynucleotide encodes a polypeptide consisting of 1190 amino acid residues in its mature form, as identified by three-letter code in SEQ ID NO: 2 (FIG. 3).

Laminin γ2-encoding nucleic acid can be prepared by applying selected techniques of gene isolation or gene synthesis as a first step. As described in more detail in the examples herein, laminin γ2 polynucleotides can be obtained by careful application of conventional gene isolation and cloning techniques such as the homologous RT(PCR) amplification technique. Gene cloning can also be conducted by extraction of total messenger RNA from an appropriate tissue source, such as skin or hair follicles, followed by conversion of message to cDNA and formation of a cDNA library in plasmidic vectors. The cDNA library is then probed using a labelled nucleic acid fragment derived from a gene believed to be highly homologous to the cDNA of interest. Hybridizing cDNA clones are further screened and positive clones are prepared for insertion into an expression vector.

Having herein provided the nucleotide sequence of a polynucleotide encoding laminin γ2 (FIG. 3), it will be appreciated that automated techniques of gene synthesis and/or amplification can be performed to generate laminin γ2-encoding DNA. In this case, because of the length of the laminin γ2-encoding DNA, application of automated synthesis may require staged gene construction in which regions of the gene are synthesized individually and then ligated in correct succession via designed overlaps.

PCR amplification may be used to directly generate all or part of the final gene. In this case, primers are synthesized which will prime the RT-(PCR) amplification of the final product, either in one piece, or in several pieces that may subsequently be ligated together via step-wise ligation of blunt ended, amplified DNA fragments, or preferentially via step-wise ligation of fragments containing naturally occurring restriction endonuclease sites.

Both cDNA or genomic DNA are suitable as templates for PCR amplification. The former may be obtained from a number of sources including commercially available cDNA libraries, single- or double-stranded cDNA, or cDNA constructed from isolated messenger RNA from a suitable tissue sample. Genomic DNA, obtained from blood or any tissue sample, may also be used as a template for the PCR-based amplification of the gene; however, the gene sequence of such genomic DNA may contain unwanted intervening sequences.

Once obtained, the laminin γ2-encoding DNA is incorporated for expression into any suitable expression vector, and host cells are transfected therewith using conventional procedures. The particular cell type selected to serve as host for production of laminin γ2 can be any of several cell types currently available in the art, including both prokaryotic and eukaryotic cell types. Chinese hamster ovary (CHO) cells for example of K1 lineage (ATCC CCL 61) including the Pro5 variant (ATCC CRL 1281); the fibroblast-like cells derived from SV40-transformed African Green monkey kidney of the CV-1 lineage (ATCC CCL 70), of the COS-1 lineage (ATCC CRL 1650) and of the COS-7 lineage (ATCC CRL 1651); murine L-cells, murine 3T3 cells (ATCC CRL 1658), murine C127 cells, human embryonic kidney cells of the 293 lineage (ATCC CRL 1573), human carcinoma cells including those of the HeLa lineage (ATCC CCL 2), and neuroblastoma cells of the lines IMR-32 (ATCC CCL 127), SK-N-MC (ATCC HTB 10) and SK-N-SH (ATCC HTB 11) all represent examples of suitable cell types for the production of mammalian laminin γ2.

A variety of gene expression systems have been developed and are now commercially available. Any one of these systems can be selected to drive expression of the laminin γ2-encoding DNA. These systems, available typically in the form of plasmidic vectors, carry expression cassettes which include DNA expression controlling sequences, which are host-recognized and enable expression of laminin γ2-encoding DNA when linked 5' thereof. Laminin γ2-encoding DNA is herein referred to as being incorporated "expressibly" into the system, and incorporated "expressibly" in a cell once successful expression from a cell is achieved. These systems further incorporate DNA sequences which terminate expression when linked 3' of the coding region. Thus, for expression in the selected cell host, there is generated a recombinant DNA expression construct in which the laminin γ2-encoding DNA is linked with expression controlling DNA sequences recognized by the host, and which include a region 5' of the laminin γ2-encoding DNA to drive expression, and a 3' region to terminate expression.

Included among the various recombinant DNA expression systems that can be used to achieve mammalian cell expression of the laminin γ2-encoding DNA are those that exploit promoters of viruses that infect mammalian cells, such as the promoter from cytomegalovirus (CMV), the Rous sarcoma virus (RSV), simian virus (SV40), murine mammary tumor virus (MMTV) and others. Also useful to drive expression are promoters such as the LTR of retroviruses, insect cell promoters, including those isolated from Drosophila which are regulated by temperature, as well as mammalian gene promoters such as those regulated by heavy metals, i.e. the metallothionein gene promoter, and other steroid-inducible promoters.

Expression systems may be selected to provide transformed cell lines that express the laminin γ2-encoding DNA in a stable manner. Suitable expression vectors will typically harbour a gene coding for a product that confers on the transformants a survival advantage to enable their subsequent selection. Genes coding for such selectable markers include the *E. coli* gpt gene which confers resistance to mycophenolic acid, the neo$^R$ gene from transposon Tn5 which confers resistance to neomycin and to the neomycin analog G418, the dhfr sequence from murine cells or *E. coli* which changes the phenotype of DHFR− cells into DHFR+ cells, and the tk gene of herpes simplex virus, which makes TK− cells phenotypically TK+ cells. Other methods of selecting for transformants may of course be used, if desired, including selection by morphological parameters, or detection of surface antigen or receptor expression. The latter can be monitored using specifically labelled antibodies and a cell-sorter, e.g. fluorescent activated.

The present invention also provides, in another of its aspects, antibody to laminin-γ2. To raise such antibodies, there may be used as immunogen either full-length laminin-γ2 or an immunogenic fragment thereof, produced in a microbial or mammalian cell host as described above or by standard peptide synthesis techniques. Regions of laminin-γ2 particularly suitable for use as immunogenic fragments include regions which are determined to have a high degree of antigenicity based on a number of factors, as would be appreciated by those of skill in the art, including for example, amino acid residue content, hydrophobicity/hydrophilicity and secondary structure. Specific examples of immunogenic fragments of laminin-γ2 suitable for generating antibodies include, but are not limited to, the region spanning residues 1–200, the region spanning residues 380–610, and the region spanning residues 800–1190.

The raising of antibodies to mammalian laminin-γ2 or to desired immunogenic fragments can be achieved, for polyclonal antibody production, using immunization protocols of conventional design, and any of a variety of mammalian hosts, such as sheep, goats and rabbits. Alternatively, for monoclonal antibody production, immunocytes such as splenocytes can be recovered from the immunized animal and fused, using hybridoma technology, to myeloma cells. The fusion cell products, i.e. hybridoma cells, are then screened by culturing in a selection medium, and cells producing the desired antibody are recovered for continuous growth, and antibody recovery. Recovered antibody can then be coupled covalently to a reporter molecule, i.e. a detectable label, such as a radiolabel, enzyme label, luminescent label or the like, using linker technology established for this purpose, to form a specific probe for laminin-γ2.

According to another aspect of the present invention, DNA or RNA encoding equine laminin γ2, and selected regions thereof, may also be used in detectably labelled form, e.g. radiolabelled or fluorescently labelled form, as hybridization probes to identify sequence-related genes existing in other mammalian genomes (or cDNA libraries). This can be done using the intact coding region, due to a high level of conservation expected between related genes, or by using a highly conserved fragment thereof, having radiolabeled nucleotides, for example, $^{32}P$ nucleotides, incorporated therein.

In a further aspect of the present invention, there is provided a method for diagnosing JEB in a horse. Although this method can be used to diagnose JEB in foals post-natally, affected animals can usually be visually diagnosed at or within days of birth. Accordingly, the method is most usefully applied prenatally, to determine whether or not an unborn foal is affected. A positive prenatal diagnosis provides a breeder with the opportunity to terminate a pregnancy that will result in the birth of a fatally affected foal. The method involves obtaining a biological sample from the horse to be diagnosed, or fetus in the case of prenatal diagnosis. For post-natal diagnosis the biological sample may be any nucleic acid or protein-containing sample, depending on the method to be used as is outlined in more detail below. Preferably, the biological sample is non-invasively obtained, including samples such as skin or hair follicles. Prenatal diagnosis is necessarily invasive. Examples of suitable biological samples for use in prenatal testing include fetal blood, skin or chorionic villosities.

In one embodiment, upon obtaining the biological sample, nucleic acid is isolated therefrom using techniques well-known to those of skill in the art. The isolated nucleic acid is then screened using specifically designed labelled probes to detect whether or not the sample contains the disease-indicating allele which is defined herein as a laminin γ2-encoding polynucleotide having a cytosine inserted at position 1368, thereby resulting in a termination codon at position 476. Using methods well-established in the art, hybridizing probes are detected and a positive diagnosis is made for an affected homozygous animal. A positive diagnosis will also result for a healthy heterozygous carrier due to the presence of the morbid allele. Accordingly, positive samples must be further analysed to determine if the animal is homozygous or heterozygous with respect to the mutated laminin γ2 gene. As is described in more detail in the specific examples that follow, direct nucleotide sequencing followed by chromatographic analysis of the genomic DNA is one way in which the homozygous and heterozygous existence of the mutated laminin γ2 alleles can be differentiated to confirm a JEB diagnosis in the homozygous case. As will be understood by those of skill in the art, the chromatographic analysis may be conducted in the absence of nucleotide sequencing in order to diagnose JEB or heterozygous carriers of JEB and to identify wild type animals which can then be selected for reproduction. Moreover, the present diagnostic method can advantageously be used, particularly post-natally to identify carriers of the mutation associated with JEB, in order that such carriers can be removed from the breeding population and thereby minimize the occurrence of JEB in offspring.

In another embodiment, a method of diagnosing JEB in horses is provided in which the protein component of the biological sample is isolated using conventional methods. The protein component is then analysed to determine whether or not it contains the laminin γ2 peptide. The absence of such a peptide indicates the presence of the mutated laminin γ2 gene (comprising a cytosine insert at nucleic acid position 1368 resulting in a premature termination codon at amino acid position 476 in the peptide) and represents a positive JEB diagnosis.

Embodiments of the present invention are described by reference to the following specific examples which are not to be construed as limiting.

EXAMPLE 1

Clinicopathological Observations and Immunochemistry Associated with JEB in Horses Clinicopathological Observations Belgian horses suffering from extensive skin blistering with severe oral cavity involvement were used for observation. Foal n° 1 was the fourth foal of a mare that had previously had an affected offspring. One day after birth, multiple ulcerations of the skin were present on the pressure points on the legs and head as shown in FIG. 1A. Ulcers were also observed on the tongue, and the mucous membrane of rostral maxillae as shown in FIG. 1D. Foal n° 2 presented multiple mucosal and epithelial erosions at birth. Multifocal, irregular areas of erosions were noted over the pressure points of the extremities, around the coronary band of all four hooves (FIG. 1B), and on the oral and conjunctival mucous membranes. An abnormal roughened enamel was present over the teeth and there was evidence of bleeding from oral erosions (FIG. 1C). In foal n° 3, multiple skin defects were noticed shortly after birth. Eight days after birth, large, extensive and confluent ulcerated areas were present over the pressure points of the body. The right front hoof had detached and the underlying lamina was exposed. The buccal mucous membranes were hyperemic. Due to the grave prognosis, the foal was euthanized and submitted for necropsy. One day after birth, foal n° 4 presented ulcerated skin lesions over the limbs and at the base of the hooves. Extensive ulcerations of the oral cavity were noted over the gingival mucosa and the soft palate. Teeth were visible and dysplastic, with white serrated edges.

The clinical observations were consistent with the characteristics of epidermolysis bullosa.

Immunochemistry

Indirect immunofluorescence analysis was performed on 5 μm sections of the frozen tongue samples using antibodies raised against the human basement membrane components and cross-reacting with the horse counterparts. Polyclonal antibody (pAb) SE85 is specific to the laminin α3 chain [Vidal, 1995]; pAb SE144 is directed against the laminin γ2 chain [Vailly, 1994] and monoclonal antibody (mAb) K140 against the laminin β3 chain [Marinkovich, 1992]. PAb GOH3 is specific to integrin α6 [Sonnenberg, 1987]; mAb233 is directed against BP180 [Hieda et al., 1992], and mAb LH7:2 is specific to the collagen VII C-terminal domain (Sigma Immunochemical). PAb anti-laminin 1 (L9393, Sigma) and pAb anti-collagen VII (10411, Institut Pasteur, Paris, France) were also used. Secondary antibodies were FITC-conjugated goat anti-mouse Ig (Dako S. A., Trappes France), and goat anti-rat IgG (Cappel, ICN Biomedicals, Orsay, France). The samples were processed as previously reported [Gache, 1996]. The tissue sections were examined using a Zeiss Axiophot microscope.

Figure 2:
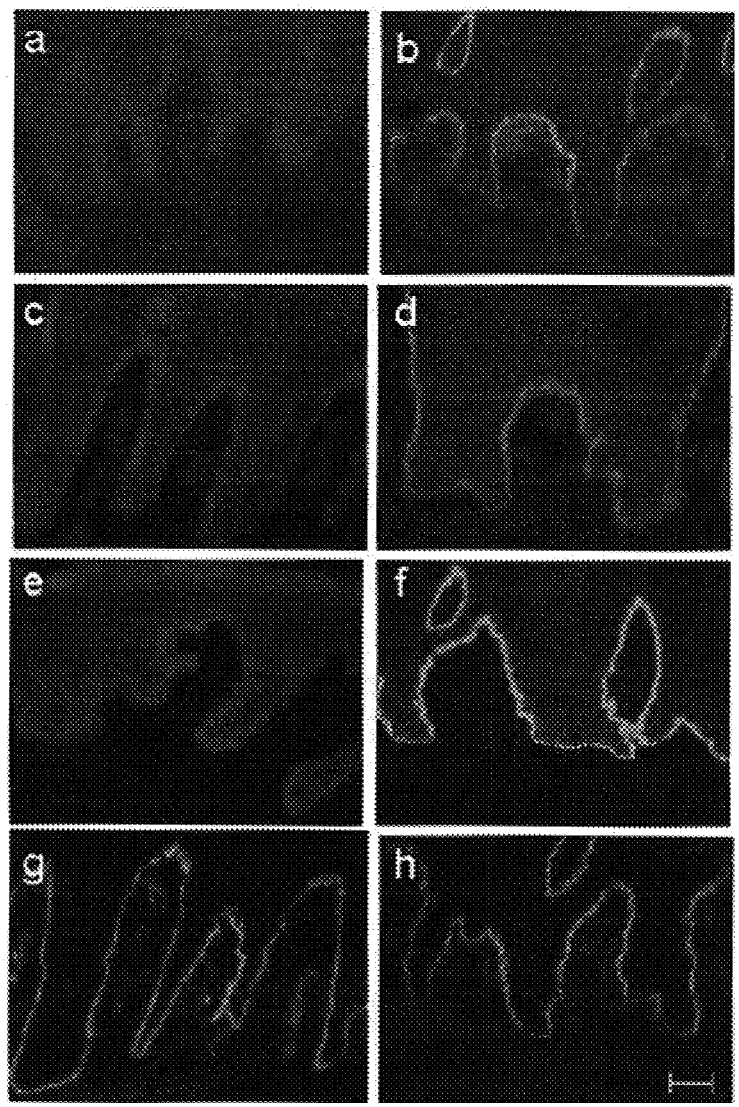
FIG. 2 illustrates the altered expression of laminin γ2 in horse JEB using an immunofluorescence analysis of frozen sections of tongue epithelia samples obtained from an affected foal (a, c, e, g) and a healthy unrelated control (b, d, f, h)

Reactivity to pAb SE144 specific to the laminin γ2 chain, was absent in the affected foals (FIG. 2a), while pAb SE85 and mAb K140 directed against the laminin α3 and β3 chains, respectively, were faintly reactive (FIGS. 2c & e). Reactivity of collagen type VII (FIGS. 2g & h), integrin α6, collagen type XVII and laminin 1, was comparable to that observed in wild-type foals (not shown). These observations suggested that expression of laminin-5 was hampered in the affected animals and indicated that Lamc2, the gene encoding the laminin γ2 chain, was involved in the etiology of the condition.

EXAMPLE 2

Isolation of the Horse Laminin γ2 cDNA

Biopsies were obtained from involved and non-involved areas of the skin and from tongue epithelia. Tissue samples were also obtained from a wild type non-related horse. The biopsies were snap frozen in liquid nitrogen and preserved at −70° C. until processing. Total RNA was purified from the frozen skin biopsies using the RNable extraction kit (Eurobio, Les Ullis, France). Genomic DNA was purified from peripheral blood following standard methods [Sambrook, 1989]

Five μg of RNA (purified from frozen skin biopsies obtained from foal n° 1) was reverse transcribed in a volume of 25 μl in the presence of 100 μ of M-MLV reverse transcriptase (GIBCO-BRL, Life Technologies, Inc.). One μl of the reaction mixture was then used in PCR amplifications to obtain overlapping cDNA fragments spanning the open reading frame of the horse laminin γ2 chain. Specifically, eight primer pairs were devised on the basis of the most conserved nucleotide sequence between the human (GenBank accession n° ZI5008 [Kallunki et al., 1992]) and mouse (GenBank n° NM 008485 [Sugiyama et al., 1995]) laminin γ2 cDNAs (not shown). Direct sequencing of the different PCR amplification products resulted in the disclosure of 82% of the horse laminin γ2 cDNA sequence. Primers specific to the horse γ2 cDNA sequence were then designed to complete and verify the sequence of the full-length γ2 cDNA (Table I). The PCR conditions were: 95° C. for 5 minutes, followed by 35 cycles at 95° C. for 40 seconds, annealing temperature (Table I) for 40 seconds, 72° C. for 40 seconds, and a final elongation for 7 minutes at 72° C. The amplification products were purified using a QIAQUICK KIT, a DNA purification kit made by Qiagen Madison, Wis., USA, and subjected to automated nucleotide sequencing using an ABI Prism Model 310 Genetic Analyzer (Perkin-Elmer, Foster City, Calif.).

To obtain the 5' end of the γ2 cDNA, the sense oligonucleotide PCR 5'L corresponding to a 5' non-coding sequence of the human laminin γ2 cDNA and the antisense primer PCR-5'R specific to the horse γ2 cDNA sequence were used to amplify a 460-bp cDNA fragment (Table I). To obtain the 3' end of the γ2 cDNA, the antisense primer RT-PCR3' containing a polyT and tag sequence was used for RT-PCR amplification of total RNA. Subsequently two PCR reactions were performed; the first using primers PCR-3'L (position 3226 on the horse γ2 cDNA) and PCR3'R, which is composed of the tag sequence. The resulting 474-bp 3'-terminal cDNA fragment was used as template for a second PCR amplification using primer PCR-3A'L (position 3325 on the horse γ2 cDNA) and primer PCR-3'R. The PCR cycling conditions, purification and sequence analysis for the isolation of the 5' and 3' ends were done as previously mentioned. Analysis, alignment, and translation of the nucleotide sequence into the amino acid sequence were performed using the software, Lalign and Cluster W.

TABLE I

Oligonucleotide primers used to amplify the horse laminin γ2 cDNA

| Primers (a) | Position (b) | Nucleotide sequence (SEQ ID No:) | Annealing Temp. (°C.) | Product size (bp) |
| --- | --- | --- | --- | --- |
| 1L | 1 | ATGCCTGCGCTCTGGCTCAG (3) | 63 | 591 |
| 1R | 592 | TGTGGCAGCTGGCGGAATGC (4) | | |
| 2L | 406 | GACTCCAAGTGTGACTGTGA (5) | 60 | 388 |
| 2R | 794 | TAGCTCACCTGTTGATTCCC (6) | | |
| 3L | 742 | CCTGTCTATTTTGTAGCTCC (7) | 57 | 670 |
| 3R | 1412 | CAGCTGAACCCATTGCGACA (8) | | |
| 4L | 1003 | GAGTATCGGAGGTTACTGCG (9) | 59 | 756 |

TABLE I-continued

Oligonucleotide primers used to amplify the horse laminin γ2 cDNA

| Primers (a) | Position (b) | Nucleotide sequence (SEQ ID No:) | Annealing Temp. (°C.) | Product size (bp) |
|---|---|---|---|---|
| 4R | 1759 | GACACTCCACAGGCTCCGAG (10) | | |
| 5L | 1477 | CGCTGTGAGCTCTGTGCTGA (11) | 65 | 422 |
| 5R | 1899 | CTCCAGGATCTGGAGCTGCT (12) | | |
| 6L | 1705 | GACAAGTGTCGAGCTTGCAA (13) | 60 | 395 |
| 6R | 2100 | TCATCATGAGGTCATCCAGG (14) | | |
| 7L | 1992 | GAGAGAAGCCCAGATTTCAC (15) | 59 | 524 |
| 7R | 2516 | GCTTCCATGTCGGTTTGCGT (16) | | |
| 8L | 2312 | CAGCCAGTAACATGGAGCAA (17) | 60 | 435 |
| 8R | 2747 | GTCTGTCTCCCATTCTTTCC (18) | | |
| 9L | 2658 | GGATGAGTTCAAGCACGTGC (19) | 57 | 514 |
| 9R | 3172 | ACAGCTCTCCTTCCACTTCT (20) | | |
| 10L | 2955 | CAAGACGAAGCAAGCAGAAG (21) | 60 | 445 |
| 10R | 3400 | GGCTGTTGATCTGAGTCTTG (22) | | |
| PCR-5'L | -197 | GTGAGTCACACCCTGAAACA (23) | 57 | 460 |
| PCR-5'R | 263 | GAGTTACAATTGCAGGGTAAAC (24) | | |
| RT-PCR 3' | — | GGCCATGCGTAGACTCTTAA(T)$_{16}$(25) | | |
| PCR-3'L | 3226 | GCAGAGGCCCAAAGAGTTG (26) | 57 | 474 |
| PCR-3'R | — | GGCCATGCGTAGACTCTTAA (27) | | |
| PCR-3A'L | 3325 | CCTGGCAGTGTGGATGAAGA (28) | 57 | 375 |

(a) L, sense primer; R, antisense primer.
(b) The position number designates the 5' end of each primer in accordance with the horse laminin γ2 cDNA sequence (to be submitted to GenBank)

The horse γ2 cDNA was determined to comprise a 3570-bp full length open reading frame, a 197-bp 5' and a 222-bp 3' untranslated region (FIG. 3). Computer assisted analysis of the nucleotide sequence revealed that the homology in the coding sequence between man and horse (89.1% identity) is higher than that between horse and mouse (83.3% identity) and that between man and mouse (83.8% identity). The 5' untranslated region (UTR) contains a GATAA box which is located −112 to −116 bp from the initiation ATG, and two AP-1 binding sites at position −129 to −135 and −170 to −176, respectively. Comparison of the 5'UTR of horse and human revealed that from position −62 to −197, which contains the regulatory motifs, the nucleotide sequence is identical, while from position −1 to −61 there is only 49% homology, with two base additions and seven base deletions. The 5' UTR of the mouse γ2 cDNA is not available to include in this comparison [Salo et al., 1999].

In the horse, the full-length γ2 cDNA encodes a polypeptide of 1190 residues which is three amino acids shorter than in man (1193 aa), and two amino acids shorter than the mouse amino acid sequence (1192). Similar to the human and mouse γ2 chain the ATG codon is followed by a signal peptide of 20 amino acids. In contrast, in the mouse only 18 hydrophobic amino acids corresponding to a putative signal peptide are found after the ATG codon. The position of the predicted signal peptide cleavage site (Ala 21) of the human γ2 chain is conserved in the horse counterpart. The horse γ2 polypeptide shows the domain structure similar to the mouse and human γ2 chains where a N-terminal short arm, rich in EGF-like repeats, extends into a long rod-like C-terminal arm. The N-terminal short arm domain V (residue 28 to 196) consists of three and a half cysteine-rich EGF-like repeats; domain IV (residues 197–381) has a globular structure and contains a single cysteine; domain III (residues 382–608) comprises four and a half EGF-like repeats, and contains the proteolytic cleavage site YSGD [Gagnoux, 2001]. Domain I/II (residues 609–1190) constitutes the rod-like long arm of the polypeptide and is formed by heptad repeats typical of the α-helical coiled-coil domains of the laminin chains. The horse γ2 chain contains 67 cysteine residues and six putative N-glycosylation sites that are conserved in the man and the mouse amino acid sequence (FIG. 4).

Alignment of the amino acid sequences revealed that domains V, IV, III of the horse and human γ2 chain are more than 90% identical, while homology between horse and mouse is 82.8%. Homology between domains I/II is significantly lower (81.3%) between horse and man, and between horse and mouse (76.6%) (Table II).

TABLE II

Sequence identity (percentage) between the domains of the horse laminin γ 2 chain and the human and mouse counterparts.

|  | V | IV | III | I/II |
|---|---|---|---|---|
| Human γ 2 | 92.3 | 94 | 93 | 81.3 |
| Murine γ 2 | 86.4 | 88.8 | 90.7 | 76.6 |

EXAMPLE 3
Identification of Genetic Mutation that Results in JEB in Horses

Figure 5:
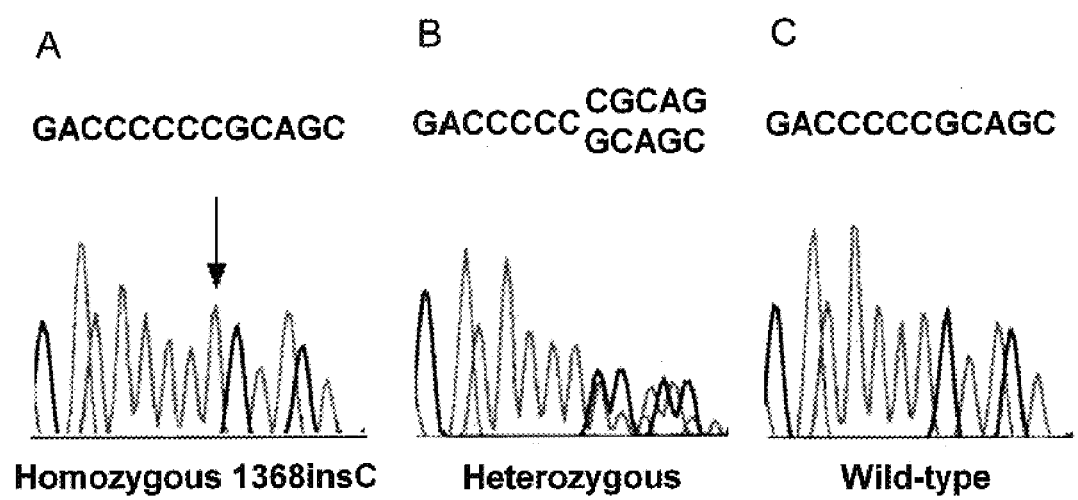
FIG. 5 provides a chromatographic comparison of the genomic sequences in which the homozygous insert mutation at position 1368 (1368insC) of the DNA sequence (panel A), the heterozygous situation for the mutation 1368insC in a carrier horse (panel B) and the wild-type DNA sequence (panel C) are shown.

Total mRNA extracted from skin biopsies of foal n° 1 was reverse transcribed in two separate reactions using in one, a universal oligo-dT and in the other, the nested primer 9R (Table I). Overlapping cDNA fragments spanning the full-length sequence of the γ2 cDNA were then amplified by PCR using the primer pairs listed in Table I. The PCR amplification products were purified and subjected to automated nucleotide sequencing. The γ2 cDNA sequence of the affected foal was compared with the wild-type nucleotide sequence using the software program Sequencher (Gene Codes Corp, Ann Arbor, Mich.). In the affected foal, the 756-bp cDNA fragment (nucleotides 1003 to 1759) obtained using primers 4L and 4R was found to contain a one-base pair insertion at position 1368 (mutation 1368insC; see FIG. 5)

Sequence chromatographic analysis following PCR amplification of the genomic DNA with the appropriate primers was used to readily distinguish homozygous (affected or wild-type) animals from heterozygous (carrier) animals. In the case of the homozygous affected horse, the chromatogram appears as a clear pattern of well-defined single peaks each of which correspond to the individual nucleotides of the sequence. The clear pattern of peaks is derived from both alleles of the nucleic acid since they are identical. At the point of the mutation there is an insertion of the nucleotide C in both alleles; this denotes the mutation as homozygous. A clear pattern also results in the case of a wild-type horse, in which both alleles are also identical. The resulting chromatogram in this case, however, represents a nucleic acid sequence which is not mutated by a "C" insertion. In the case of the heterozygous situation, the chromatogram shows two superposed sequences starting at the site of the insertion mutation, and corresponding to one allele having the inserted C (therefore, the sequence is shifted by one nucleotide), while the other is the wild type allele (see FIG. 5).

This mutation, designated 1368insC, causes a shift in the open reading frame of the γ2 messenger RNA and results in a downstream premature termination codon (TGA) at residue 476 which is in the N-terminal portion of domain III, 41 residues downstream of the proteolytic cleavage site of the chain.

Identification of the mutation 1368insC at the genomic level was performed by PCR amplification of a 170-bp DNA fragment (nucleotides 1291–1461 of γ2 cDNA sequence) using genomic DNA as a template and primers: (sense) 5'-TGTTACTCAGGGGATGAGAA-3' (SEQ ID No: 29—nucleotides 1291 to 1310 of the γ2 cDNA sequence) and (antisense) 5'-CTGGGGGCAGTTATTGCAC-3' (SEQ ID No: 30—the reverse compliment of the sequence from 1443 to 1461 of the γ2 cDNA sequence), which correspond to the sequence within exon 10 of the human LAMC2 gene. PCR cycling conditions were: 5 minutes at 95° C., followed by 30 seconds at 95° C., 30 seconds at 56° C., 30 seconds at 72° C. (35 cycles), and extension for 7 minutes at 72° C. After purification, the amplification product was submitted to automated nucleotide sequencing.

Figure 6:
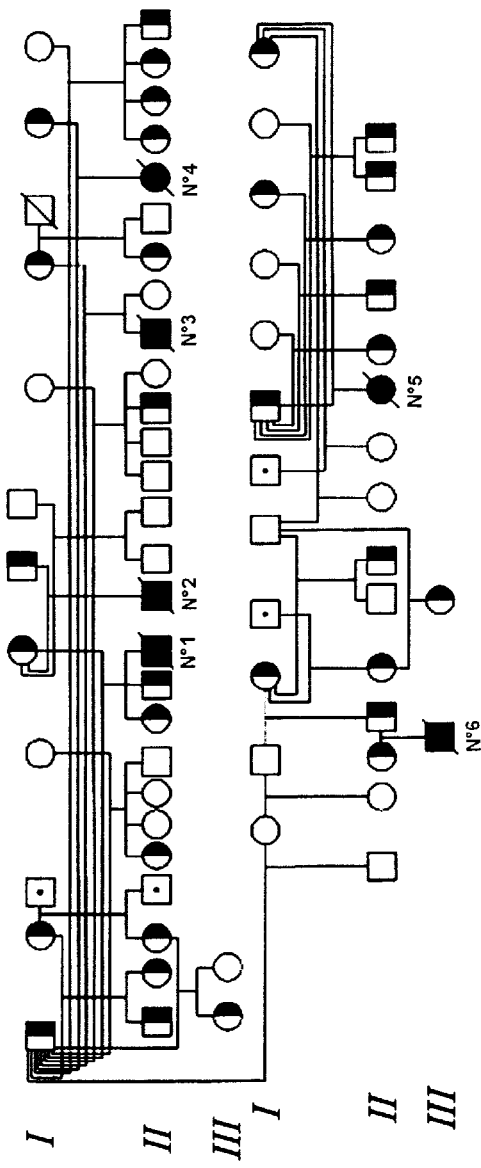
FIG. 6 illustrates the inheritance of the laminin γ2 mutant allele in Belgian horses.

The presence of the homozygous mutation 1368insC in the other affected foals was confirmed. When the phenotypically healthy dam and sire of the affected foals were tested for the presence of this mutation, they were found to be heterozygous carriers. To assess the frequency of this mutation in the Belgian horse, samples for genomic DNA extraction were obtained from various breeding farms in the USA and Canada. Results demonstrated that 50% of the screened animals (n=132) were healthy carriers, which confirmed the Mendelian transmission of the mutation 1368insC (FIG. 6).

References

Bruckner-Tuderman L, Guscetti F, and Ehrensperger F. 1991. Animal model for dermolytic mechanobullous disease: sheep with recessive dystrophic epidermolysis bullosa lack collagen VII. *J Invest Dermatol.* 96:452–8.

Engel, J., I. Hunter, T. Schulthess, K. Beck, T. W. Dixon, and D. A. Parry. 1991. Assembly of laminin isoforms by triple- and double-stranded coiled-coil structures. *Biochem Soc Trans.* 19:839–43.

Fine, J. D., R. A. Eady, E. A. Bauer, R. A. Briggaman, L. Bruckner-Tuderman, A. Christiano, A. Heagerty, H. Hintner, M. F. Jonkman, J. McGrath, J. McGuire, A. Moshell, H. Shimizu, G. Tadini, and J. Uitto. 2000. Revised classification system for inherited epidermolysis bullosa: Report of the Second International Consensus Meeting on diagnosis and classification of epidermolysis bullosa. *J Am Acad Dermatol.* 42:1051–66.

Fuchs, E. 1992. Genetic skin disorders of keratin. *J Invest Dermatol.* 99:671–4.

Gache, Y., S. Chavanas, J. P. Lacour, G. Wiche, K. Owaribe, G. Meneguzzi, and J. P. Ortonne. 1996. Defective expression of plectin/HD1 in epidermolysis bullosa simplex with muscular dystrophy. *J Clin Invest.* 97:2289–98.

Gagnoux-Palacios, L., M. Allegra, F. Spirito, O. Pommeret, C. Romero, J. P. Ortonne, and G. Meneguzzi. 2001. The short arm of the laminin gamma2 chain plays a pivotal role in the incorporation of laminin 5 into the extracellular matrix and in cell adhesion. *J Cell Biol.* 153:835–50.

Hieda, Y., Y. Nishizawa, J. Uematsu, and K. Owaribe. 1992. Identification of a new hemidesmosomal protein, HD1: a major, high molecular mass component of isolated hemidesmosomes. *J Cell Biol.* 116:1497–1506.

Kallunki, P., K. Sainio, R. Eddy, M. Byers, T. Kallunki, H. Sariola, K. Beck, H. Hirvonen, T. B. Shows, and K. Tryggvason. 1992. A truncated laminin chain homologous to the B2 chain: structure, spatial expression, and chromosomal assignment. *J Cell Biol.* 119:679–93.

Marinkovich, M. P., G. P. Lunstrum, and R. E. Burgeson. 1992. The anchoring filament protein kalinin is synthesized and secreted as a high molecular weight precursor. *J Biol Chem.* 267:17900–6.

Pulkkinen, L., and J. Uitto. 1999. Mutation analysis and molecular genetics of epidermolysis bullosa. *Matrix Biol.* 18:29–42.

Salo, S., H. Haakana, S. Kontusaari, E. Hujanen, T. Kallunki, and K. Tryggvason. 1999. Laminin-5 promotes adhesion and migration of epithelial cells: identification of a migration-related element in the gamma2 chain gene (LAMC2) with activity in transgenic mice. *Matrix Biol.* 18:197–210.

Sambrook, J., E. F. Fritsch, and T. Maniatis. 1989. Molecular cloning. A laboratory manual.

Sonnenberg, A., H. Janssen, F. Hogervorst, J. Calafat, and J. Hilgers. 1987. A complex of platelet glycoproteins Ic and IIa identified by a rat monoclonal antibody. *J Biol Chem.* 262:10376–83.

Sugiyama, S., A. Utani, S. Yamada, C. A. Kozak, and Y. Yamada. 1995. Cloning and expression of the mouse laminin gamma 2 (B2t) chain, a subunit of epithelial cell laminin. *Eur J Biochem.* 228:120–8.

Uitto, J., and A. M. Christiano. 1993. Dystrophic forms of epidermolysis bullosa. *Semin Dermatol.* 12:191–201.

Vailly, J., P. Verrando, M. F. Champliaud, D. Gerecke, D. W. Wagman, C. Baudoin, D. Aberdam, R. Burgeson, E. Bauer, and J. P. Ortonne. 1994. The 100-kDa chain of nicein/kalinin is a laminin B2 chain variant. *Eur J Biochem.* 219:209–18.

Vidal, F., D. Aberdam, C. Miquel, A. M. Christiano, L. Pulkkinen, J. Uitto, J. P. Ortonne, and G. Meneguzzi. 1995. Integrin beta 4 mutations associated with junctional epidermolysis bullosa with pyloric atresia. *Nat Genet.* 10:229–34.

---

We claim:

1. A method of diagnosing epidermolysis bullosa in a horse comprising the steps of:
   1) obtaining a biological sample from the horse;
   2) isolating nucleic acid therefrom and amplifying laminin γ2-encoding nucleic acid using appropriate sense and antisense primers; and
   3) analysing the amplified nucleic acid to identify the presence of mutated laminin γ2-encoding nucleic acid having a cytosine insert at a position corresponding to position 1368 of SEQ ID No. 1, wherein the homozygous presence of said mutated laminin γ2-encoding nucleic acid indicates a diagnosis of epidermolysis bullosa.

2. A method as defined in claim 1, wherein the sense primers used to amplify the laminin γ2-encoding nucleic acid comprises the nucleotide sequence, 5'-TGTTACTCAGGGGATGAGAA-3' (SEQ ID No: 29) and the antisense primer comprises the nucleotide sequence, 5'-CTGGGGGCAGTTATTGCAC-3' (SEQ ID No: 30).

3. A method as defined in claim 1, wherein the amplified nucleic acid is chromatographically analysed to identify the heterozygous presence of the mutated laminin γ2-encoding nucleic acid.

4. A kit for diagnosing epidermolysis bullosa in horses comprising the nucleic acid primers 5'-TGTTACTCAGGGGATGAGAA-3' (SEQ ID No: 29) and (antisense) 5'-CTGGGGGCAGTTATTGCAC-3' (SEQ ID No: 30).

5. A method as defined in claim 1, wherein the sample is obtained from an unborn foal.

6. The method of claim 1 wherein the mutated laminin γ2-encoding nucleic acid has a cytosine insert at position 1368 of SEQ ID No. 1.

* * * * *

SEQUENCE LISTING

<160> NUMBER OF SEQ ID NOS: 32

<210> SEQ ID NO 1
<211> LENGTH: 3989
<212> TYPE: DNA
<213> ORGANISM: equine
<220> FEATURE:
<221> NAME/KEY: CDS
<222> LOCATION: (198)...(3767)
<223> OTHER INFORMATION:

<400> SEQUENCE: 1

```
tgggtcctcc ttattcacag gtgagtcaca ccctgaaaca caggctctct tcctgtcagg        60
actgagtcag gtagaagagt cgataaaacc acctgatcaa ggaaaaggaa ggcacagcgg       120
agcgcagagt gagaactccc agcggcgagg cgccgggcag cgacccctgc agcggcggac       180
cgcgcgccgg cctggcc atg cct gcg ctc tgg ctg agc tgc tac ctc tgc         230
                Met Pro Ala Leu Trp Leu Ser Cys Tyr Leu Cys
                 1               5                  10 ttc tcg ctc ctc ctg ccc gca gcc cgg gcc acc tcc ggg agg gaa gtc         278
Phe Ser Leu Leu Leu Pro Ala Ala Arg Ala Thr Ser Gly Arg Glu Val
            15                  20                  25 tgt gat tgc aac ggg aag tcc agg caa tgc atc ttt gac cag gaa ctt         326
Cys Asp Cys Asn Gly Lys Ser Arg Gln Cys Ile Phe Asp Gln Glu Leu
        30                  35                  40 cac aaa cag aca gga aat gga ttc cgc tgc ctc aac tgc aat gac aac         374
His Lys Gln Thr Gly Asn Gly Phe Arg Cys Leu Asn Cys Asn Asp Asn
    45                  50                  55 act gat ggc atc cac tgc gag agg tgc aag gca gga ttt tac cga cag         422
Thr Asp Gly Ile His Cys Glu Arg Cys Lys Ala Gly Phe Tyr Arg Gln
60                  65                  70                  75 aga gaa agg gac cgc tgt tta ccc tgc aat tgt aac tct aaa ggt tct         470
Arg Glu Arg Asp Arg Cys Leu Pro Cys Asn Cys Asn Ser Lys Gly Ser
                80                  85                  90 ctt agc gct cga tgt gac aac tct gga cgg tgc agc tgt aag cca ggt         518
Leu Ser Ala Arg Cys Asp Asn Ser Gly Arg Cys Ser Cys Lys Pro Gly
            95                 100                 105 gtg aca gga gac agg tgt gac cga tgt ctg ccc ggc ttc cac aca ctc         566
Val Thr Gly Asp Arg Cys Asp Arg Cys Leu Pro Gly Phe His Thr Leu
        110                 115                 120 act gat gct ggg tgc gcc caa gac caa agg ctg cta gac tcc aag tgt         614
Thr Asp Ala Gly Cys Ala Gln Asp Gln Arg Leu Leu Asp Ser Lys Cys
    125                 130                 135 gac tgt gac cca gct ggc atc tca ggg ccc tgt gac tca ggc cgc tgt         662
Asp Cys Asp Pro Ala Gly Ile Ser Gly Pro Cys Asp Ser Gly Arg Cys
140                 145                 150                 155 gtc tgc aag ccg gct gtc act gga gag cgc tgt gat agg tgt cga cca         710
Val Cys Lys Pro Ala Val Thr Gly Glu Arg Cys Asp Arg Cys Arg Pro
                160                 165                 170
```

| | | |
|---|---|---|
| ggt tac tat cac ctg gat ggg gga aac cct cag ggc tgt acc cag tgt<br>Gly Tyr Tyr His Leu Asp Gly Gly Asn Pro Gln Gly Cys Thr Gln Cys<br>175 180 185 | 758 |
| ttt tgc tat ggg cat tcc gcc agc tgc cac agc tct ggg gac tac agt<br>Phe Cys Tyr Gly His Ser Ala Ser Cys His Ser Ser Gly Asp Tyr Ser<br>190 195 200 | 806 |
| gtc cat aaa atc atc tct gcc ttc cat caa gat gtt gat ggc tgg aag<br>Val His Lys Ile Ile Ser Ala Phe His Gln Asp Val Asp Gly Trp Lys<br>205 210 215 | 854 |
| gct gtc caa aga aac ggg tct cct gca aag ctc cag tgg tca cag cgc<br>Ala Val Gln Arg Asn Gly Ser Pro Ala Lys Leu Gln Trp Ser Gln Arg<br>220 225 230 235 | 902 |
| cat cgg gat ata ttt agc tca gca cga cga tca gac cct gtc tat ttt<br>His Arg Asp Ile Phe Ser Ser Ala Arg Arg Ser Asp Pro Val Tyr Phe<br>240 245 250 | 950 |
| gta gct cct gcc aaa ttt ctt ggg aat caa cag gtg agc tac ggg caa<br>Val Ala Pro Ala Lys Phe Leu Gly Asn Gln Gln Val Ser Tyr Gly Gln<br>255 260 265 | 998 |
| agc cta tct ttt gac tac cgt gtg gat agg gga ggc aga cac cca tct<br>Ser Leu Ser Phe Asp Tyr Arg Val Asp Arg Gly Gly Arg His Pro Ser<br>270 275 280 | 1046 |
| gcc cat gac gtg atc ctg gaa ggt gct ggt cta cgg atc aca gct ccc<br>Ala His Asp Val Ile Leu Glu Gly Ala Gly Leu Arg Ile Thr Ala Pro<br>285 290 295 | 1094 |
| ttg atg cca ctt agc aag aca ctg cct tgt ggg atc acc aag act tac<br>Leu Met Pro Leu Ser Lys Thr Leu Pro Cys Gly Ile Thr Lys Thr Tyr<br>300 305 310 315 | 1142 |
| aca ttc aga tta aat gaa cat cca agc agt aat tgg agc ccc cag cta<br>Thr Phe Arg Leu Asn Glu His Pro Ser Ser Asn Trp Ser Pro Gln Leu<br>320 325 330 | 1190 |
| agt tac ttt gag tat cgg agg tta ctg cgg aac ctc aca gcc ctg cgg<br>Ser Tyr Phe Glu Tyr Arg Arg Leu Leu Arg Asn Leu Thr Ala Leu Arg<br>335 340 345 | 1238 |
| atc cga gct acc tac gga gaa tac agt act ggg tac att gac aac gtg<br>Ile Arg Ala Thr Tyr Gly Glu Tyr Ser Thr Gly Tyr Ile Asp Asn Val<br>350 355 360 | 1286 |
| acc ttg att tca gcc cgc ccc gtt tct gga gcc cca gcg ccc tgg gtt<br>Thr Leu Ile Ser Ala Arg Pro Val Ser Gly Ala Pro Ala Pro Trp Val<br>365 370 375 | 1334 |
| gaa caa tgt gta tgc cct gtt ggc tac aag ggg cag ttc tgc cag gat<br>Glu Gln Cys Val Cys Pro Val Gly Tyr Lys Gly Gln Phe Cys Gln Asp<br>380 385 390 395 | 1382 |
| tgt gct tcc ggc tac aaa aga gat tca gcc aga ctg gga cct ttt ggc<br>Cys Ala Ser Gly Tyr Lys Arg Asp Ser Ala Arg Leu Gly Pro Phe Gly<br>400 405 410 | 1430 |
| acc tgt att cca tgt aac tgc caa ggg gga ggg gcc tgc gat cca gac<br>Thr Cys Ile Pro Cys Asn Cys Gln Gly Gly Gly Ala Cys Asp Pro Asp<br>415 420 425 | 1478 |
| aca gga gac tgt tac tca ggg gat gag aac cct gac atc cct gag tgt<br>Thr Gly Asp Cys Tyr Ser Gly Asp Glu Asn Pro Asp Ile Pro Glu Cys<br>430 435 440 | 1526 |
| gct gac tgc ccc att ggt ttc tac aac gat cca caa gac ccc gc agc<br>Ala Asp Cys Pro Ile Gly Phe Tyr Asn Asp Pro Gln Asp Pro Arg Ser<br>445 450 455 | 1574 |
| tgc aag ccg tgc ccc tgt cgc aat ggg ttc agc tgc tcc gtg atg cct<br>Cys Lys Pro Cys Pro Cys Arg Asn Gly Phe Ser Cys Ser Val Met Pro<br>460 465 470 475 | 1622 |
| gag aca gag gag gtg gtg tgc aat aac tgc ccc cag ggt gtc act ggt<br>Glu Thr Glu Glu Val Val Cys Asn Asn Cys Pro Gln Gly Val Thr Gly | 1670 |

-continued

|  |  |  | 480 |  |  |  | 485 |  |  |  | 490 |  |  |  |
|---|---|---|---|---|---|---|---|---|---|---|---|---|---|---|
| gcc | cgc | tgt | gag | ctc | tgt | gct | gat | ggc | tat | ttt | ggg | gac | ccc | ttc | ggg | 1718 |
| Ala | Arg | Cys | Glu | Leu | Cys | Ala | Asp | Gly | Tyr | Phe | Gly | Asp | Pro | Phe | Gly |
|  |  |  | 495 |  |  |  | 500 |  |  |  | 505 |  |  |  | gaa cgt ggc cca gtg agg cct tgt cag ccc tgt cag tgc aac aac aac    1766
Glu Arg Gly Pro Val Arg Pro Cys Gln Pro Cys Gln Cys Asn Asn Asn
            510                 515                 520 gtg gac cct agt gcc tcc ggg aac tgt gac cgc ctg aca ggc agg tgt    1814
Val Asp Pro Ser Ala Ser Gly Asn Cys Asp Arg Leu Thr Gly Arg Cys
525                 530                 535 ctg aag tgc atc cac aac aca gct ggg tca cac tgt gac cag tgc aaa    1862
Leu Lys Cys Ile His Asn Thr Ala Gly Val His Cys Asp Gln Cys Lys
540                 545                 550                 555 gca ggc tac tat ggg gac ccg ttg gct ccc aat cca gca gac aag tgt    1910
Ala Gly Tyr Tyr Gly Asp Pro Leu Ala Pro Asn Pro Ala Asp Lys Cys
            560                 565                 570 cga gct tgc aac tgc aac cca gtg ggc tcg gag cct gtg gag tgt cga    1958
Arg Ala Cys Asn Cys Asn Pro Val Gly Ser Glu Pro Val Glu Cys Arg
575                 580                 585 agt gat ggc agc tgt gtt tgc aag cca ggc ttt ggt ggc ctc agc tgt    2006
Ser Asp Gly Ser Cys Val Cys Lys Pro Gly Phe Gly Gly Leu Ser Cys
            590                 595                 600 gag cat gcg gca ctg acc agc tgt cca gct tgc tat aat caa gtg aag    2054
Glu His Ala Ala Leu Thr Ser Cys Pro Ala Cys Tyr Asn Gln Val Lys
605                 610                 615 gtt cag atg gat cag ttt atg cag cag ctc cag atc ctg gag gcc ctg    2102
Val Gln Met Asp Gln Phe Met Gln Gln Leu Gln Ile Leu Glu Ala Leu
620                 625                 630                 635 att tcg aag gct cag ggt gga gca gta ccc aac gca gag ctg gaa ggc    2150
Ile Ser Lys Ala Gln Gly Gly Ala Val Pro Asn Ala Glu Leu Glu Gly
            640                 645                 650 agg atg cag cag gct gag cag gcc ctt cgg gac att ctg aga gaa gcc    2198
Arg Met Gln Gln Ala Glu Gln Ala Leu Arg Asp Ile Leu Arg Glu Ala
655                 660                 665 cag att tca caa gat gct gtt aga tcc ttc aat ctc cgg gtg gcc aag    2246
Gln Ile Ser Gln Asp Ala Val Arg Ser Phe Asn Leu Arg Val Ala Lys
            670                 675                 680 gca agg act caa gag aat agc tac cgg gac cgc ctg gat gac ctc aag    2294
Ala Arg Thr Gln Glu Asn Ser Tyr Arg Asp Arg Leu Asp Asp Leu Lys
685                 690                 695 atg act gtg gaa aga gtt cgg gcc ctg ggc agt cag tat cag aac caa    2342
Met Thr Val Glu Arg Val Arg Ala Leu Gly Ser Gln Tyr Gln Asn Gln
700                 705                 710                 715 gtt cag gat act cgc agg ctc atc act cag atg cgc ctg agc ctg gag    2390
Val Gln Asp Thr Arg Arg Leu Ile Thr Gln Met Arg Leu Ser Leu Glu
            720                 725                 730 gaa agt gag gct tcc ctg caa aac acc aac att cct cct tca gag cac    2438
Glu Ser Glu Ala Ser Leu Gln Asn Thr Asn Ile Pro Pro Ser Glu His
735                 740                 745 tac gtg ggg cca aat ggc ttt aaa agt ctg gct cag gag gcc acg aga    2486
Tyr Val Gly Pro Asn Gly Phe Lys Ser Leu Ala Gln Glu Ala Thr Arg
            750                 755                 760 ttg gca gac agc cat gtt cag tca gcc agt aac atg gag caa ctg gca    2534
Leu Ala Asp Ser His Val Gln Ser Ala Ser Asn Met Glu Gln Leu Ala
765                 770                 775 aag gaa acc cag gag tat tcc aaa gag ctg atg tca ctg gtg cgc gag    2582
Lys Glu Thr Gln Glu Tyr Ser Lys Glu Leu Met Ser Leu Val Arg Glu
780                 785                 790                 795 gct ctg cag gaa gga gga gga agc ggc agc ctg gac gga gcc gtg gtg    2630

-continued

```
                Ala Leu Gln Glu Gly Gly Gly Ser Gly Ser Leu Asp Gly Ala Val Val
                                800                 805                 810 caa agg ctt gtg gga aaa ttg cag aaa act aaa tct ctg gcc cag gag                    2678
Gln Arg Leu Val Gly Lys Leu Gln Lys Thr Lys Ser Leu Ala Gln Glu
            815                 820                 825 ttg tcg agg gag gcc acg caa acc gac atg gaa gca gat agg tct tat                    2726
Leu Ser Arg Glu Ala Thr Gln Thr Asp Met Glu Ala Asp Arg Ser Tyr
        830                 835                 840 cag cat agt ctc cac ctt ctc aat tcc gtg tct cag att cag gga gtc                    2774
Gln His Ser Leu His Leu Leu Asn Ser Val Ser Gln Ile Gln Gly Val
    845                 850                 855 aat gat cag tcc ttg cag gta gaa gcg aag agg ctc aga caa aaa gct                    2822
Asn Asp Gln Ser Leu Gln Val Glu Ala Lys Arg Leu Arg Gln Lys Ala
860                 865                 870                 875 gat tct ctc tca aac cgt gtg act aag cat atg gat gag ttc aag cac                    2870
Asp Ser Leu Ser Asn Arg Val Thr Lys His Met Asp Glu Phe Lys His
                880                 885                 890 gtg caa agc aat ctg gga aac tgg gaa gaa gaa acc cgg cag ctc tta                    2918
Val Gln Ser Asn Leu Gly Asn Trp Glu Glu Glu Thr Arg Gln Leu Leu
            895                 900                 905 cag aat gga aag aat ggg aga cag aca tca gat cag ctg ctt tcc cgt                    2966
Gln Asn Gly Lys Asn Gly Arg Gln Thr Ser Asp Gln Leu Leu Ser Arg
        910                 915                 920 gcc aac ctt gct aaa agc aga gcc caa gaa gca cta agt atg ggc aat                    3014
Ala Asn Leu Ala Lys Ser Arg Ala Gln Glu Ala Leu Ser Met Gly Asn
    925                 930                 935 gcc act ttt tat gaa gtt gag aac atc tta aag aat ctc aga gag ttt                    3062
Ala Thr Phe Tyr Glu Val Glu Asn Ile Leu Lys Asn Leu Arg Glu Phe
940                 945                 950                 955 gac ctg cag gtt gga gat aaa aga gca gaa gct gaa gag gcc atg aag                    3110
Asp Leu Gln Val Gly Asp Lys Arg Ala Glu Ala Glu Glu Ala Met Lys
                960                 965                 970 aga ctc tcc tac atc agc cag aag gtt gca ggt gcc agt gac aag acg                    3158
Arg Leu Ser Tyr Ile Ser Gln Lys Val Ala Gly Ala Ser Asp Lys Thr
            975                 980                 985 aag caa gca gaa gca gcc ctg ggc agt gct gct gcc gac gcc cag agg                    3206
Lys Gln Ala Glu Ala Ala Leu Gly Ser Ala Ala Ala Asp Ala Gln Arg
        990                 995                 1000 gca aag aat gca gcc agg gag gcc ctg gag atc tct ggc aag ata gaa                    3254
Ala Lys Asn Ala Ala Arg Glu Ala Leu Glu Ile Ser Gly Lys Ile Glu
    1005                1010                1015 cag gag ata gga ggt ctg aac ttg gaa gcc aat gtg aca gca gat gga                    3302
Gln Glu Ile Gly Gly Leu Asn Leu Glu Ala Asn Val Thr Ala Asp Gly
1020                1025                1030                1035 gcc ttg gcc atg gag aag gga ctg gcc act ctg aaa agt gag atg aga                    3350
Ala Leu Ala Met Glu Lys Gly Leu Ala Thr Leu Lys Ser Glu Met Arg
                1040                1045                1050 gaa gtg gaa gga gag ctg tca agg aag gag cag gag ttt gac atg gat                    3398
Glu Val Glu Gly Glu Leu Ser Arg Lys Glu Gln Glu Phe Asp Met Asp
            1055                1060                1065 atg gac gca gtg cag atg gta att gca gag gcc caa aga gtt gaa aac                    3446
Met Asp Ala Val Gln Met Val Ile Ala Glu Ala Gln Arg Val Glu Asn
        1070                1075                1080 aga gcc aag aat gct gga gtt acg atc caa gac aca ctc aac aca ttg                    3494
Arg Ala Lys Asn Ala Gly Val Thr Ile Gln Asp Thr Leu Asn Thr Leu
    1085                1090                1095 gat ggc atc cta cac cta ata gac cag cct ggc agt gtg gat gaa gag                    3542
Asp Gly Ile Leu His Leu Ile Asp Gln Pro Gly Ser Val Asp Glu Glu
1100                1105                1110                1115
```

```
                                                              -continued agg ctg atc tta ctg gag cag aag ctt ttc cga gcc aag act cag atc       3590
Arg Leu Ile Leu Leu Glu Gln Lys Leu Phe Arg Ala Lys Thr Gln Ile
            1120                1125                1130 aac agc cag cta cgg ccc ttg atg tca gag ctg gaa gag agg gca cat       3638
Asn Ser Gln Leu Arg Pro Leu Met Ser Glu Leu Glu Glu Arg Ala His
        1135                1140                1145 cgg cag aag ggc cac ctc cgt ttc ctg gag act agc ata gat ggg att       3686
Arg Gln Lys Gly His Leu Arg Phe Leu Glu Thr Ser Ile Asp Gly Ile
    1150                1155                1160 ctg gct gat gtg aag aac ctg gag aac atc agg gac aac ctg ccc ccg       3734
Leu Ala Asp Val Lys Asn Leu Glu Asn Ile Arg Asp Asn Leu Pro Pro
1165                1170                1175 ggc tgc tac aat acc cag gct ctt gag caa cag tgaagctgcc ttagagattt    3787
Gly Cys Tyr Asn Thr Gln Ala Leu Glu Gln Gln
1180                1185                1190 ctcaaccaag gttcttggga ttcagaccta gctgccttag agatttctca accaaggttc     3847
ttgggattca gacctcaggg ctcaggagcc cgcatgcggg tggggtggga tgggaatatt    3907
tgaatatgtt gaatgcgtgt gctcaggccc cagtgaacct gatcccatcc ctgagacctc    3967
ggccagataa atgtctttat tg                                              3989

<210> SEQ ID NO 2
<211> LENGTH: 1190
<212> TYPE: PRT
<213> ORGANISM: Equine
<220> FEATURE:
<223> OTHER INFORMATION:

<400> SEQUENCE: 2

Met Pro Ala Leu Trp Leu Ser Cys Tyr Leu Cys Phe Ser Leu Leu Leu
1               5                   10                  15

Pro Ala Ala Arg Ala Thr Ser Gly Arg Glu Val Cys Asp Cys Asn Gly
            20                  25                  30

Lys Ser Arg Gln Cys Ile Phe Asp Gln Glu Leu His Lys Gln Thr Gly
        35                  40                  45

Asn Gly Phe Arg Cys Leu Asn Cys Asn Asp Asn Thr Asp Gly Ile His
    50                  55                  60

Cys Glu Arg Cys Lys Ala Gly Phe Tyr Arg Gln Arg Glu Arg Asp Arg
65                  70                  75                  80

Cys Leu Pro Cys Asn Cys Asn Ser Lys Gly Ser Leu Ser Ala Arg Cys
                85                  90                  95

Asp Asn Ser Gly Arg Cys Ser Cys Lys Pro Gly Val Thr Gly Asp Arg
            100                 105                 110

Cys Asp Arg Cys Leu Pro Gly Phe His Thr Leu Thr Asp Ala Gly Cys
        115                 120                 125

Ala Gln Asp Gln Arg Leu Leu Asp Ser Lys Cys Asp Cys Asp Pro Ala
    130                 135                 140

Gly Ile Ser Gly Pro Cys Asp Ser Gly Arg Cys Val Cys Lys Pro Ala
145                 150                 155                 160

Val Thr Gly Glu Arg Cys Asp Arg Cys Arg Pro Gly Tyr Tyr His Leu
                165                 170                 175

Asp Gly Gly Asn Pro Gln Gly Cys Thr Gln Cys Phe Cys Tyr Gly His
            180                 185                 190

Ser Ala Ser Cys His Ser Ser Gly Asp Tyr Ser Val His Lys Ile Ile
        195                 200                 205

Ser Ala Phe His Gln Asp Val Asp Gly Trp Lys Ala Val Gln Arg Asn
    210                 215                 220
```

```
Gly Ser Pro Ala Lys Leu Gln Trp Ser Gln Arg His Arg Asp Ile Phe
225                 230                 235                 240

Ser Ser Ala Arg Arg Ser Asp Pro Val Tyr Phe Val Ala Pro Ala Lys
            245                 250                 255

Phe Leu Gly Asn Gln Gln Val Ser Tyr Gly Gln Ser Leu Ser Phe Asp
            260                 265                 270

Tyr Arg Val Asp Arg Gly Arg His Pro Ser Ala His Asp Val Ile
        275                 280                 285

Leu Glu Gly Ala Gly Leu Arg Ile Thr Ala Pro Leu Met Pro Leu Ser
    290                 295                 300

Lys Thr Leu Pro Cys Gly Ile Thr Lys Thr Tyr Thr Phe Arg Leu Asn
305                 310                 315                 320

Glu His Pro Ser Ser Asn Trp Ser Pro Gln Leu Ser Tyr Phe Glu Tyr
                325                 330                 335

Arg Arg Leu Leu Arg Asn Leu Thr Ala Leu Arg Ile Arg Ala Thr Tyr
            340                 345                 350

Gly Glu Tyr Ser Thr Gly Tyr Ile Asp Asn Val Thr Leu Ile Ser Ala
        355                 360                 365

Arg Pro Val Ser Gly Ala Pro Ala Pro Trp Val Glu Gln Cys Val Cys
    370                 375                 380

Pro Val Gly Tyr Lys Gly Gln Phe Cys Gln Asp Cys Ala Ser Gly Tyr
385                 390                 395                 400

Lys Arg Asp Ser Ala Arg Leu Gly Pro Phe Gly Thr Cys Ile Pro Cys
            405                 410                 415

Asn Cys Gln Gly Gly Ala Cys Asp Pro Asp Thr Gly Asp Cys Tyr
            420                 425                 430

Ser Gly Asp Glu Asn Pro Asp Ile Pro Glu Cys Ala Asp Cys Pro Ile
        435                 440                 445

Gly Phe Tyr Asn Asp Pro Gln Asp Pro Arg Ser Cys Lys Pro Cys Pro
    450                 455                 460

Cys Arg Asn Gly Phe Ser Cys Ser Val Met Pro Glu Thr Glu Glu Val
465                 470                 475                 480

Val Cys Asn Asn Cys Pro Gln Gly Val Thr Gly Ala Arg Cys Glu Leu
            485                 490                 495

Cys Ala Asp Gly Tyr Phe Gly Asp Pro Phe Gly Glu Arg Gly Pro Val
        500                 505                 510

Arg Pro Cys Gln Pro Cys Gln Cys Asn Asn Asn Val Asp Pro Ser Ala
    515                 520                 525

Ser Gly Asn Cys Asp Arg Leu Thr Gly Arg Cys Leu Lys Cys Ile His
    530                 535                 540

Asn Thr Ala Gly Val His Cys Asp Gln Cys Lys Ala Gly Tyr Tyr Gly
545                 550                 555                 560

Asp Pro Leu Ala Pro Asn Pro Ala Asp Lys Cys Arg Ala Cys Asn Cys
            565                 570                 575

Asn Pro Val Gly Ser Glu Pro Val Glu Cys Arg Ser Asp Gly Ser Cys
            580                 585                 590

Val Cys Lys Pro Gly Phe Gly Gly Leu Ser Cys Glu His Ala Ala Leu
        595                 600                 605

Thr Ser Cys Pro Ala Cys Tyr Asn Gln Val Lys Val Gln Met Asp Gln
    610                 615                 620

Phe Met Gln Gln Leu Gln Ile Leu Glu Ala Leu Ile Ser Lys Ala Gln
625                 630                 635                 640
```

```
Gly Gly Ala Val Pro Asn Ala Glu Leu Glu Gly Arg Met Gln Gln Ala
            645                 650                 655
Glu Gln Ala Leu Arg Asp Ile Leu Arg Glu Ala Gln Ile Ser Gln Asp
            660                 665                 670
Ala Val Arg Ser Phe Asn Leu Arg Val Ala Lys Ala Arg Thr Gln Glu
            675                 680                 685
Asn Ser Tyr Arg Asp Arg Leu Asp Asp Leu Lys Met Thr Val Glu Arg
            690                 695                 700
Val Arg Ala Leu Gly Ser Gln Tyr Gln Asn Gln Val Gln Asp Thr Arg
705                 710                 715                 720
Arg Leu Ile Thr Gln Met Arg Leu Ser Leu Glu Ser Glu Ala Ser
            725                 730                 735
Leu Gln Asn Thr Asn Ile Pro Pro Ser Glu His Tyr Val Gly Pro Asn
            740                 745                 750
Gly Phe Lys Ser Leu Ala Gln Glu Ala Thr Arg Leu Ala Asp Ser His
            755                 760                 765
Val Gln Ser Ala Ser Asn Met Glu Gln Leu Ala Lys Glu Thr Gln Glu
            770                 775                 780
Tyr Ser Lys Glu Leu Met Ser Leu Val Arg Glu Ala Leu Gln Glu Gly
785                 790                 795                 800
Gly Gly Ser Gly Ser Leu Asp Gly Ala Val Gln Arg Leu Val Gly
            805                 810                 815
Lys Leu Gln Lys Thr Lys Ser Leu Ala Gln Glu Leu Ser Arg Glu Ala
            820                 825                 830
Thr Gln Thr Asp Met Glu Ala Asp Arg Ser Tyr Gln His Ser Leu His
            835                 840                 845
Leu Leu Asn Ser Val Ser Gln Ile Gln Gly Val Asn Asp Gln Ser Leu
850                 855                 860
Gln Val Glu Ala Lys Arg Leu Arg Gln Lys Ala Asp Ser Leu Ser Asn
865                 870                 875                 880
Arg Val Thr Lys His Met Asp Glu Phe Lys His Val Gln Ser Asn Leu
            885                 890                 895
Gly Asn Trp Glu Glu Thr Arg Gln Leu Leu Gln Asn Gly Lys Asn
            900                 905                 910
Gly Arg Gln Thr Ser Asp Gln Leu Leu Ser Arg Ala Asn Leu Ala Lys
            915                 920                 925
Ser Arg Ala Gln Glu Ala Leu Ser Met Gly Asn Ala Thr Phe Tyr Glu
            930                 935                 940
Val Glu Asn Ile Leu Lys Asn Leu Arg Glu Phe Asp Leu Gln Val Gly
945                 950                 955                 960
Asp Lys Arg Ala Glu Ala Glu Glu Ala Met Lys Arg Leu Ser Tyr Ile
            965                 970                 975
Ser Gln Lys Val Ala Gly Ala Ser Asp Lys Thr Lys Gln Ala Glu Ala
            980                 985                 990
Ala Leu Gly Ser Ala Ala Asp Ala Gln Arg Ala Lys Asn Ala Ala
            995                 1000                1005
Arg Glu Ala Leu Glu Ile Ser Gly Lys Ile Glu Gln Glu Ile Gly Gly
            1010                1015                1020
Leu Asn Leu Glu Ala Asn Val Thr Ala Asp Gly Ala Leu Ala Met Glu
1025                1030                1035                1040
Lys Gly Leu Ala Thr Leu Lys Ser Glu Met Arg Glu Val Glu Gly Glu
            1045                1050                1055
Leu Ser Arg Lys Glu Gln Glu Phe Asp Met Asp Met Asp Ala Val Gln
```

```
              1060           1065           1070
Met Val Ile Ala Glu Ala Gln Arg Val Glu Asn Arg Ala Lys Asn Ala
        1075           1080           1085

Gly Val Thr Ile Gln Asp Thr Leu Asn Thr Leu Asp Gly Ile Leu His
        1090           1095           1100

Leu Ile Asp Gln Pro Gly Ser Val Asp Glu Arg Leu Ile Leu Leu
1105           1110           1115           1120

Glu Gln Lys Leu Phe Arg Ala Lys Thr Gln Ile Asn Ser Gln Leu Arg
                1125           1130           1135

Pro Leu Met Ser Glu Leu Glu Glu Arg Ala His Arg Gln Lys Gly His
        1140           1145           1150

Leu Arg Phe Leu Glu Thr Ser Ile Asp Gly Ile Leu Ala Asp Val Lys
        1155           1160           1165

Asn Leu Glu Asn Ile Arg Asp Asn Leu Pro Pro Gly Cys Tyr Asn Thr
        1170           1175           1180

Gln Ala Leu Glu Gln Gln
1185           1190

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
atgcctgcgc tctggctcag                                            20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
tgtggcagct ggcggaatgc                                            20

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
gactccaagt gtgactgtga                                            20

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
tagctcacct gttgattccc                                            20

<210> SEQ ID NO 7
<211> LENGTH: 20
<212> TYPE: DNA
<213> ORGANISM: Artificial Sequence
```

```
<220> FEATURE:
<223> OTHER INFORMATION: primer

<400> SEQUENCE: 7
cctgtctatt ttgtagctcc                                               20

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
cagctgaacc cattgcgaca                                               20

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
gagtatcgga ggttactgcg                                               20

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
gacactccac aggctccgag                                               20

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
cgctgtgagc tctgtgctga                                               20

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
ctccaggatc tggagctgct                                               20

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
gacaagtgtc gagcttgcaa                                               20
```

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
tcatcatgag gtcatccagg                                       20

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
gagagaagcc cagatttcac                                       20

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
gcttccatgt cggtttgcgt                                       20

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
cagccagtaa catggagcaa                                       20

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
gtctgtctcc cattctttcc                                       20

<210> SEQ ID NO 19
<211> LENGTH: 20
<212> TYPE: DNA
<213> ORGANISM: Artificial Sequence
<220> FEATURE:
<223> OTHER INFORMATION: primer

<400> SEQUENCE: 19
ggatgagttc aagcacgtgc                                       20

<210> SEQ ID NO 20
<211> LENGTH: 20
<212> TYPE: DNA
<213> ORGANISM: Artificial Sequence
<220> FEATURE:
<223> OTHER INFORMATION: primer

```
<400> SEQUENCE: 20
acagctctcc ttccacttct                                              20

<210> SEQ ID NO 21
<211> LENGTH: 20
<212> TYPE: DNA
<213> ORGANISM: Artificial Sequence
<220> FEATURE:
<223> OTHER INFORMATION: primer

<400> SEQUENCE: 21
caagacgaag caagcagaag                                              20

<210> SEQ ID NO 22
<211> LENGTH: 20
<212> TYPE: DNA
<213> ORGANISM: Artificial Sequence
<220> FEATURE:
<223> OTHER INFORMATION: primer

<400> SEQUENCE: 22
ggctgttgat ctgagtcttg                                              20

<210> SEQ ID NO 23
<211> LENGTH: 20
<212> TYPE: DNA
<213> ORGANISM: Artificial Sequence
<220> FEATURE:
<223> OTHER INFORMATION: primer

<400> SEQUENCE: 23
gtgagtcaca ccctgaaaca                                              20

<210> SEQ ID NO 24
<211> LENGTH: 22
<212> TYPE: DNA
<213> ORGANISM: Artificial Sequence
<220> FEATURE:
<223> OTHER INFORMATION: primer

<400> SEQUENCE: 24
gagttacaat tgcagggtaa ac                                           22

<210> SEQ ID NO 25
<211> LENGTH: 36
<212> TYPE: DNA
<213> ORGANISM: Artificial Sequence
<220> FEATURE:
<223> OTHER INFORMATION: primer

<400> SEQUENCE: 25
ggccatgcgt agactcttaa tttttttttt tttttt                            36

<210> SEQ ID NO 26
<211> LENGTH: 19
<212> TYPE: DNA
<213> ORGANISM: Artificial Sequence
<220> FEATURE:
<223> OTHER INFORMATION: primer

<400> SEQUENCE: 26
gcagaggccc aaagagttg                                               19

<210> SEQ ID NO 27
```

-continued

```
<211> LENGTH: 20
<212> TYPE: DNA
<213> ORGANISM: Artificial Sequence
<220> FEATURE:
<223> OTHER INFORMATION: primer

<400> SEQUENCE: 27
ggccatgcgt agactcttaa                                              20

<210> SEQ ID NO 28
<211> LENGTH: 20
<212> TYPE: DNA
<213> ORGANISM: Artificial Sequence
<220> FEATURE:
<223> OTHER INFORMATION: primer

<400> SEQUENCE: 28
cctggcagtg tggatgaaga                                              20

<210> SEQ ID NO 29
<211> LENGTH: 20
<212> TYPE: DNA
<213> ORGANISM: Artificial Sequence
<220> FEATURE:
<223> OTHER INFORMATION: primer

<400> SEQUENCE: 29
tgttactcag gggatgagaa                                              20

<210> SEQ ID NO 30
<211> LENGTH: 19
<212> TYPE: DNA
<213> ORGANISM: Artificial Sequence
<220> FEATURE:
<223> OTHER INFORMATION: primer

<400> SEQUENCE: 30
ctgggggcag ttattgcac                                               19

<210> SEQ ID NO 31
<211> LENGTH: 1193
<212> TYPE: PRT
<213> ORGANISM: human
<220> FEATURE:
<223> OTHER INFORMATION:

<400> SEQUENCE: 31
```

Met Pro Ala Leu Trp Leu Gly Cys Cys Leu Cys Phe Ser Leu Leu Leu
 1               5                   10                  15

Pro Ala Ala Arg Ala Thr Ser Arg Arg Glu Val Cys Asp Cys Asn Gly
            20                  25                  30

Lys Ser Arg Gln Cys Ile Phe Asp Arg Glu Leu His Arg Gln Thr Gly
        35                  40                  45

Asn Gly Phe Arg Cys Leu Asn Cys Asn Asp Asn Thr Asp Gly Ile His
    50                  55                  60

Cys Glu Lys Cys Lys Asn Gly Phe Tyr Arg His Arg Glu Arg Asp Arg
65                  70                  75                  80

Cys Leu Pro Cys Asn Cys Asn Ser Lys Gly Ser Leu Ser Ala Arg Cys
                85                  90                  95

Asp Asn Ser Gly Arg Cys Ser Cys Lys Pro Gly Val Thr Gly Ala Arg
            100                 105                 110

Cys Asp Arg Cys Leu Pro Gly Phe His Met Leu Thr Asp Ala Gly Cys
        115                 120                 125

-continued

```
Thr Gln Asp Gln Arg Leu Leu Asp Ser Lys Cys Asp Cys Asp Pro Ala
    130                 135                 140
Gly Ile Ala Gly Pro Cys Asp Ala Gly Arg Cys Val Cys Lys Pro Ala
145                 150                 155                 160
Val Thr Gly Glu Arg Cys Asp Arg Cys Arg Ser Gly Tyr Tyr Asn Leu
                165                 170                 175
Asp Gly Gly Asn Pro Glu Gly Cys Thr Gln Cys Phe Cys Tyr Gly His
            180                 185                 190
Ser Ala Ser Cys Arg Ser Ser Ala Glu Tyr Ser Val His Lys Ile Thr
        195                 200                 205
Ser Thr Phe His Gln Asp Val Asp Gly Trp Lys Ala Val Gln Arg Asn
    210                 215                 220
Gly Ser Pro Ala Lys Leu Gln Trp Ser Gln Arg His Gln Asp Val Phe
225                 230                 235                 240
Ser Ser Ala Gln Arg Leu Asp Pro Val Tyr Phe Val Ala Pro Ala Lys
                245                 250                 255
Phe Leu Gly Asn Gln Gln Val Ser Tyr Gly Gln Ser Leu Ser Phe Asp
            260                 265                 270
Tyr Arg Val Asp Arg Gly Gly Arg His Pro Ser Ala His Asp Val Ile
        275                 280                 285
Leu Glu Gly Ala Gly Leu Arg Ile Thr Ala Pro Leu Met Pro Leu Gly
    290                 295                 300
Lys Thr Leu Pro Cys Gly Leu Thr Lys Thr Tyr Thr Phe Arg Leu Asn
305                 310                 315                 320
Glu His Pro Ser Asn Asn Trp Ser Pro Gln Leu Ser Tyr Phe Glu Tyr
                325                 330                 335
Arg Arg Leu Leu Arg Asn Leu Thr Ala Leu Arg Ile Arg Ala Thr Tyr
            340                 345                 350
Gly Glu Tyr Ser Thr Gly Tyr Ile Asp Asn Val Thr Leu Ile Ser Ala
        355                 360                 365
Arg Pro Val Ser Gly Ala Pro Ala Pro Trp Val Glu Gln Cys Ile Cys
    370                 375                 380
Pro Val Gly Tyr Lys Gly Gln Phe Cys Gln Asp Cys Ala Ser Gly Tyr
385                 390                 395                 400
Lys Arg Asp Ser Ala Arg Leu Gly Pro Phe Gly Thr Cys Ile Pro Cys
                405                 410                 415
Asn Cys Gln Gly Gly Gly Ala Cys Asp Pro Asp Thr Gly Asp Cys Tyr
            420                 425                 430
Ser Gly Asp Glu Asn Pro Asp Ile Glu Cys Ala Asp Cys Pro Ile Gly
        435                 440                 445
Phe Tyr Asn Asp Pro His Asp Pro Arg Ser Cys Lys Pro Cys Pro Cys
    450                 455                 460
His Asn Gly Phe Ser Cys Ser Val Met Pro Glu Thr Glu Glu Val Val
465                 470                 475                 480
Cys Asn Asn Cys Pro Pro Gly Val Thr Gly Ala Arg Cys Glu Leu Cys
                485                 490                 495
Ala Asp Gly Tyr Phe Gly Asp Pro Phe Gly Glu His Gly Pro Val Arg
            500                 505                 510
Pro Cys Gln Pro Cys Gln Cys Asn Asn Asn Val Asp Pro Ser Ala Ser
        515                 520                 525
Gly Asn Cys Asp Arg Leu Thr Gly Arg Cys Leu Lys Cys Ile His Asn
    530                 535                 540
```

```
Thr Ala Gly Ile Tyr Cys Asp Gln Cys Lys Ala Gly Tyr Phe Gly Asp
545                 550                 555                 560

Pro Leu Ala Pro Asn Pro Ala Asp Lys Cys Arg Ala Cys Asn Cys Asn
                565                 570                 575

Pro Met Gly Ser Glu Pro Val Gly Cys Arg Ser Asp Gly Thr Cys Val
                580                 585                 590

Cys Lys Pro Gly Phe Gly Gly Pro Asn Cys Glu His Gly Ala Phe Ser
            595                 600                 605

Cys Pro Ala Cys Tyr Asn Gln Val Lys Ile Gln Met Asp Gln Phe Met
            610                 615                 620

Gln Gln Leu Gln Arg Met Glu Ala Leu Ile Ser Lys Ala Gln Gly Gly
625                 630                 635                 640

Asp Gly Val Val Pro Asp Thr Glu Leu Glu Gly Arg Met Gln Gln Ala
                645                 650                 655

Glu Gln Ala Leu Gln Asp Ile Leu Arg Asp Ala Gln Ile Ser Glu Gly
                660                 665                 670

Ala Ser Arg Ser Leu Gly Leu Gln Leu Ala Lys Val Arg Ser Gln Glu
            675                 680                 685

Asn Ser Tyr Gln Ser Arg Leu Asp Asp Leu Lys Met Thr Val Glu Arg
            690                 695                 700

Val Arg Ala Leu Gly Ser Gln Tyr Gln Asn Arg Val Arg Asp Thr His
705                 710                 715                 720

Arg Leu Ile Thr Gln Met Gln Leu Ser Leu Ala Glu Ser Glu Ala Ser
                725                 730                 735

Leu Gly Asn Thr Asn Ile Pro Ala Ser Asp His Tyr Val Gly Pro Asn
                740                 745                 750

Gly Phe Lys Ser Leu Ala Gln Glu Ala Thr Arg Leu Ala Glu Ser His
            755                 760                 765

Val Glu Ser Ala Ser Asn Met Glu Gln Leu Thr Arg Glu Thr Glu Asp
770                 775                 780

Tyr Ser Lys Gln Ala Leu Ser Leu Val Arg Lys Ala Leu His Glu Gly
785                 790                 795                 800

Val Gly Ser Gly Ser Gly Ser Pro Asp Gly Ala Val Val Gln Gly Leu
                805                 810                 815

Val Glu Lys Leu Glu Lys Thr Lys Ser Leu Ala Gln Gln Leu Thr Arg
            820                 825                 830

Glu Ala Thr Gln Ala Glu Ile Glu Ala Asp Arg Ser Tyr Gln His Ser
            835                 840                 845

Leu Arg Leu Leu Asp Ser Val Ser Arg Leu Gln Gly Val Ser Asp Gln
850                 855                 860

Ser Phe Gln Val Glu Glu Ala Lys Arg Ile Lys Gln Lys Ala Asp Ser
865                 870                 875                 880

Leu Ser Thr Leu Val Thr Arg His Met Asp Glu Phe Lys Arg Thr Gln
                885                 890                 895

Lys Asn Leu Gly Asn Trp Lys Glu Glu Ala Gln Gln Leu Leu Gln Asn
            900                 905                 910

Gly Lys Ser Gly Arg Glu Lys Ser Asp Gln Leu Leu Ser Arg Ala Asn
            915                 920                 925

Leu Ala Lys Ser Arg Ala Gln Glu Ala Leu Ser Met Gly Asn Ala Thr
            930                 935                 940

Phe Tyr Glu Val Glu Ser Ile Leu Lys Asn Leu Arg Glu Phe Asp Leu
945                 950                 955                 960

Gln Val Asp Asn Arg Lys Ala Glu Ala Glu Glu Ala Met Lys Arg Leu
```

-continued

```
                  965                 970                 975
Ser Tyr Ile Ser Gln Lys Val Ser Asp Ala Ser Asp Lys Thr Gln Gln
            980                 985                 990

Ala Glu Arg Ala Leu Gly Ser Ala Ala Asp Ala Gln Arg Ala Lys
        995                1000                1005

Asn Gly Ala Gly Glu Ala Leu Glu Ile Ser Ser Glu Ile Glu Gln Glu
       1010                1015                1020

Ile Gly Ser Leu Asn Leu Glu Ala Asn Val Thr Ala Asp Gly Ala Leu
1025                1030                1035                1040

Ala Met Glu Lys Gly Leu Ala Ser Leu Lys Ser Glu Met Arg Glu Val
           1045                1050                1055

Glu Gly Glu Leu Glu Arg Lys Glu Leu Glu Phe Asp Thr Asn Met Asp
       1060                1065                1070

Ala Val Gln Met Val Ile Thr Glu Ala Gln Lys Val Asp Thr Arg Ala
       1075                1080                1085

Lys Asn Ala Gly Val Thr Ile Gln Asp Thr Leu Asn Thr Leu Asp Gly
       1090                1095                1100

Leu Leu His Leu Met Asp Gln Pro Leu Ser Val Asp Glu Gly Leu
1105                1110                1115                1120

Val Leu Leu Glu Gln Lys Leu Ser Arg Ala Lys Thr Gln Ile Asn Ser
           1125                1130                1135

Gln Leu Arg Pro Met Met Ser Glu Leu Glu Glu Arg Ala Arg Gln Gln
       1140                1145                1150

Arg Gly His Leu His Leu Leu Glu Thr Ser Ile Asp Gly Ile Leu Ala
       1155                1160                1165

Asp Val Lys Asn Leu Glu Asn Ile Arg Asp Asn Leu Pro Pro Gly Cys
       1170                1175                1180

Tyr Asn Thr Gln Ala Leu Glu Gln Gln
1185                1190
```

```
<210> SEQ ID NO 32
<211> LENGTH: 1192
<212> TYPE: PRT
<213> ORGANISM: murine
<220> FEATURE:
<223> OTHER INFORMATION:

<400> SEQUENCE: 32
```

```
Met Pro Ala Leu Trp Leu Ser Cys Cys Leu Gly Val Ala Leu Leu Leu
 1               5                  10                  15

Pro Ala Ser Gln Ala Thr Ser Arg Arg Glu Val Cys Asp Cys Asn Gly
            20                  25                  30

Lys Ser Arg Gln Cys Val Phe Asp Gln Glu Leu His Arg Gln Ala Gly
        35                  40                  45

Ser Gly Phe Arg Cys Leu Asn Cys Asn Asp Asn Thr Ala Gly Val His
    50                  55                  60

Cys Glu Arg Ser Arg Glu Gly Phe Tyr Gln His Gln Ser Lys Ser Arg
65                  70                  75                  80

Cys Leu Pro Cys Asn Cys His Ser Lys Gly Ser Leu Ser Ala Gly Cys
                85                  90                  95

Asp Asn Ser Gly Gln Cys Arg Cys Lys Pro Gly Val Thr Gly Gln Arg
           100                 105                 110

Cys Asp Gln Cys Gln Pro Gly Phe His Met Leu Thr Asp Ala Gly Cys
       115                 120                 125

Thr Arg Asp Gln Gly Gln Leu Asp Ser Lys Cys Asp Cys Asp Pro Ala
```

```
                130             135             140
Gly Ile Ser Gly Pro Cys Asp Ser Gly Arg Cys Val Cys Lys Pro Ala
145                 150                 155                 160

Val Thr Gly Glu Arg Cys Asp Arg Cys Arg Pro Arg Asp Tyr His Leu
                165                 170                 175

Asp Arg Ala Asn Pro Glu Gly Cys Thr Gln Cys Phe Cys Tyr Gly His
                180                 185                 190

Ser Ala Ser Cys His Ala Ser Ala Asp Phe Ser Val His Lys Ile Thr
                195                 200                 205

Ser Thr Phe Ser Gln Asp Val Asp Gly Trp Lys Ala Val Gln Arg Asn
    210                 215                 220

Gly Ala Pro Ala Lys Leu His Trp Ser Gln Arg His Arg Asp Val Phe
225                 230                 235                 240

Ser Ser Ala Arg Arg Ser Asp Pro Val Tyr Phe Val Ala Pro Ala Lys
                245                 250                 255

Phe Leu Gly Asn Gln Gln Val Ser Tyr Gly Gln Ser Leu Ser Phe Asp
                260                 265                 270

Tyr Arg Val Asp Arg Gly Gly Arg Gln Pro Ser Ala Tyr Asp Val Ile
    275                 280                 285

Leu Glu Gly Ala Gly Leu Gln Ile Arg Ala Pro Leu Met Ala Pro Gly
    290                 295                 300

Lys Thr Leu Pro Cys Gly Ile Thr Lys Thr Tyr Thr Phe Arg Leu Asn
305                 310                 315                 320

Glu His Pro Ser Ser His Trp Ser Pro Gln Leu Ser Tyr Phe Glu Tyr
                325                 330                 335

Arg Arg Leu Leu Arg Asn Leu Thr Ala Leu Leu Met Ile Arg Ala Thr
                340                 345                 350

Tyr Gly Glu Tyr Ser Thr Gly Tyr Ile Asp Asn Val Thr Leu Val Ser
    355                 360                 365

Ala Arg Pro Val Leu Gly Ala Pro Ala Pro Trp Val Glu Arg Cys Val
    370                 375                 380

Cys Leu Leu Gly Tyr Lys Gly Gln Phe Cys Gln Glu Cys Ala Ser Gly
385                 390                 395                 400

Tyr Lys Arg Asp Ser Ala Arg Leu Gly Ala Phe Gly Ala Cys Val Pro
                405                 410                 415

Cys Asn Cys Gln Gly Glu Gly Ala Cys Asp Pro Asp Thr Gly Asp Cys
                420                 425                 430

Tyr Ser Gly Asp Glu Asn Pro Asp Ile Glu Cys Ala Asp Cys Pro Ile
    435                 440                 445

Gly Phe Tyr Asn Asp Pro His Asp Pro Arg Ser Cys Lys Pro Cys Pro
    450                 455                 460

Cys His Asn Gly Phe Ser Cys Ser Val Met Pro Glu Thr Glu Glu Val
465                 470                 475                 480

Val Cys Asn Asn Cys Pro Pro Gly Val Thr Gly Ala Arg Cys Glu Leu
                485                 490                 495

Cys Ala Asp Gly Phe Phe Gly Asp Pro Phe Gly Glu His Gly Pro Val
                500                 505                 510

Arg Pro Cys Gln Arg Cys Gln Cys Asn Asn Asn Val Asp Pro Asn Ala
                515                 520                 525

Ser Gly Asn Cys Asp Gln Leu Thr Gly Arg Cys Leu Lys Cys Ile Tyr
    530                 535                 540

Asn Thr Ala Gly Val Tyr Cys Asp Gln Cys Lys Ala Gly Tyr Phe Gly
545                 550                 555                 560
```

-continued

```
Asp Pro Leu Ala Pro Asn Pro Ala Asp Lys Cys Arg Ala Cys Asn Cys
            565                 570                 575

Ser Pro Met Gly Ala Glu Pro Gly Glu Cys Arg Gly Asp Gly Ser Cys
            580                 585                 590

Val Cys Lys Pro Gly Phe Gly Ala Phe Asn Cys Asp His Ala Ala Leu
            595                 600                 605

Thr Ser Cys Pro Ala Cys Tyr Asn Gln Val Lys Ile Gln Met Asp Gln
            610                 615                 620

Phe Thr Gln Gln Leu Gln Ser Leu Glu Ala Leu Val Ser Lys Ala Gln
625                 630                 635                 640

Gly Gly Gly Gly Gly Thr Val Pro Val Gln Leu Glu Gly Arg Ile
                645                 650                 655

Glu Gln Ala Glu Gln Ala Leu Gln Asp Ile Leu Gly Glu Ala Gln Ile
                660                 665                 670

Ser Glu Gly Ala Met Arg Ala Val Ala Val Arg Leu Ala Lys Ala Arg
                675                 680                 685

Ser Gln Glu Asn Asp Tyr Lys Thr Arg Leu Asp Asp Leu Lys Met Thr
            690                 695                 700

Ala Glu Arg Ile Arg Ala Leu Gly Ser Gln His Gln Asn Arg Val Gln
705                 710                 715                 720

Asp Thr Ser Arg Leu Ile Ser Gln Met Arg Leu Ser Leu Ala Gly Ser
                725                 730                 735

Glu Ala Leu Leu Glu Asn Thr Asn Ile His Ser Ser Glu His Tyr Val
                740                 745                 750

Gly Pro Asn Asp Phe Lys Ser Leu Ala Gln Glu Ala Thr Arg Lys Ala
            755                 760                 765

Asp Ser His Ala Glu Ser Ala Asn Ala Met Lys Gln Leu Ala Arg Glu
            770                 775                 780

Thr Glu Asp Tyr Ser Lys Gln Ala Leu Ser Leu Ala Arg Lys Leu Leu
785                 790                 795                 800

Ser Gly Gly Gly Ser Gly Ser Trp Asp Ser Ser Val Val Gln Gly
                805                 810                 815

Leu Met Gly Lys Leu Glu Lys Thr Lys Ser Leu Ser Gln Gln Leu Ser
                820                 825                 830

Leu Glu Gly Thr Gln Ala Asp Ile Glu Ala Asp Arg Ser Tyr Gln His
            835                 840                 845

Ser Leu Arg Leu Leu Asp Ser Ala Ser Gln Leu Gln Gly Val Ser Asp
850                 855                 860

Leu Ser Phe Gln Val Glu Ala Lys Arg Ile Arg Gln Lys Ala Asp Ser
865                 870                 875                 880

Leu Ser Asn Leu Val Thr Arg Gln Thr Asp Ala Phe Thr Arg Val Arg
                885                 890                 895

Asn Asn Leu Gly Asn Trp Glu Lys Glu Thr Arg Gln Leu Leu Gln Thr
                900                 905                 910

Gly Lys Asp Arg Arg Gln Thr Ser Asp Gln Leu Leu Ser Arg Ala Asn
            915                 920                 925

Leu Ala Lys Asn Arg Ala Gln Glu Ala Leu Ser Met Gly Asn Ala Thr
            930                 935                 940

Phe Tyr Glu Val Glu Asn Ile Leu Lys Asn Leu Arg Glu Phe Asp Leu
945                 950                 955                 960

Gln Val Glu Asp Arg Lys Ala Glu Ala Glu Glu Ala Met Lys Arg Leu
                965                 970                 975
```

―continued

```
Ser Ser Ile Ser Gln Lys Val Ala Asp Ala Ser Asp Lys Thr Gln Gln
            980             985             990

Ala Glu Thr Ala Leu Gly Ser Ala Thr Ala Asp Thr Gln Arg Ala Lys
        995             1000            1005

Asn Ala Ala Arg Glu Ala Leu Glu Ile Ser Ser Glu Ile Glu Leu Glu
    1010            1015            1020

Ile Gly Ser Leu Asn Leu Glu Ala Asn Val Thr Ala Asp Gly Ala Leu
1025            1030            1035            1040

Ala Met Glu Lys Gly Thr Ala Thr Leu Lys Ser Glu Met Arg Glu Met
                1045            1050            1055

Ile Glu Leu Ala Arg Lys Glu Leu Glu Phe Asp Thr Asp Lys Asp Thr
            1060            1065            1070

Val Gln Leu Val Ile Thr Glu Ala Gln Gln Ala Asp Ala Arg Ala Thr
        1075            1080            1085

Ser Ala Gly Val Thr Ile Gln Asp Thr Leu Asn Thr Leu Asp Gly Ile
    1090            1095            1100

Leu His Leu Ile Asp Gln Pro Gly Ser Val Asp Glu Glu Gly Met Met
1105            1110            1115            1120

Leu Leu Glu Gln Gly Leu Phe Gln Ala Lys Thr Gln Ile Asn Ser Arg
                1125            1130            1135

Leu Arg Pro Leu Met Ser Asp Leu Glu Glu Arg Val Arg Arg Gln Arg
            1140            1145            1150

Asn His Leu His Leu Leu Glu Thr Ser Ile Asp Gly Ile Leu Ala Asp
        1155            1160            1165

Val Lys Asn Leu Glu Asn Ile Arg Asp Asn Leu Pro Pro Gly Cys Tyr
    1170            1175            1180

Asn Thr Gln Ala Leu Glu Gln Gln
1185            1190
```